(12) United States Patent
Itoh et al.

(10) Patent No.: US 9,217,071 B2
(45) Date of Patent: Dec. 22, 2015

(54) FLUORESCENT COMPOUND, METHOD FOR PRODUCING THE SAME, AND FLUORESCENT RESIN COMPOSITION

(71) Applicant: Shin-Etsu Chemical Co., Ltd., Tokyo (JP)

(72) Inventors: Yusuke Itoh, Joetsu (JP); Ayumu Kiyomori, Joetsu (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 14/178,417

(22) Filed: Feb. 12, 2014

(65) Prior Publication Data

US 2014/0235774 A1 Aug. 21, 2014

(30) Foreign Application Priority Data

Feb. 18, 2013 (JP) ................................. 2013-029045

(51) Int. Cl.
*C08K 5/544* (2006.01)
*C09K 11/06* (2006.01)
*C07F 7/08* (2006.01)

(52) U.S. Cl.
CPC ............... *C08K 5/544* (2013.01); *C07F 7/0854* (2013.01); *C09K 11/06* (2013.01); *C09K 2211/1007* (2013.01); *C09K 2211/1014* (2013.01)

(58) Field of Classification Search
CPC ..... C08K 5/544; C07F 7/0818; C07F 7/0854; C09K 11/06
USPC .......................................... 524/188; 556/424
See application file for complete search history.

(56) References Cited

U.S. PATENT DOCUMENTS 7,887,932 B2  2/2011 Lyu et al.

FOREIGN PATENT DOCUMENTS

| EP | 2457917 A1 | 5/2012 |
|---|---|---|
| JP | 58-065440 | 4/1983 |
| JP | 09-034142 | 2/1997 |
| JP | 11-119458 | 4/1999 |
| JP | 2005-346011 | 12/2005 |
| JP | 2007-063273 | 3/2007 |
| JP | 2007-169535 | 7/2007 |
| JP | 2007-192905 | 8/2007 |
| JP | 2008-218983 | 9/2008 |

OTHER PUBLICATIONS

Haberkorn et al. "Template-Based Preparation of Free-Standing Semiconducting Polymeric Nanorod Arrays on Conductive Substrates", *Applied Materials & Interfaces* 2(6):1573-1580 (2010).

Kamino et al. "Liquid Triarylamines: The Scope and Limitations of Piers-Rubinsztajn Conditions for Obtaining Triarylamine-Siloxane Hybrid Materials", *J. Org. Chem.* 77:1663-1674 (2012).

Li et al. "Air-Stable, Cross-Linkable, Hole-Injecting/Transporting Interlayers for Improved Charge Injection in Organic Light-Emitting Diodes", *Chem. Mater.* 20:4873-4882 (2008).

Extended European Search Report corresponding to European Application No. 14155284.4 issued May 9, 2014.

Kamino et al. "Controlling the Physical and Electrochemical Properties of Arylamines Through the Use of Simple Silyl Ethers: Liguid, Waxy and Glassy Arylamines", Silicon 3:125-137 (2011).

Maegawa et al. "Preparation of functionalized aryl(diallyl)ethoxysilanes and their palladium-catalyzed coupling reactions giving sol-gel precursors", Tetrahedron 63:11467-11474 (2007).

Office Action corresponding to Japanese Application No. 2013-029045 dated Oct. 23, 2015.

*Primary Examiner* — John Uselding

(74) *Attorney, Agent, or Firm* — Myers Bigel Sibley & Sajovec, P.A.

(57) ABSTRACT

The present invention provides a fluorescent compound represented by the following general formula (1):

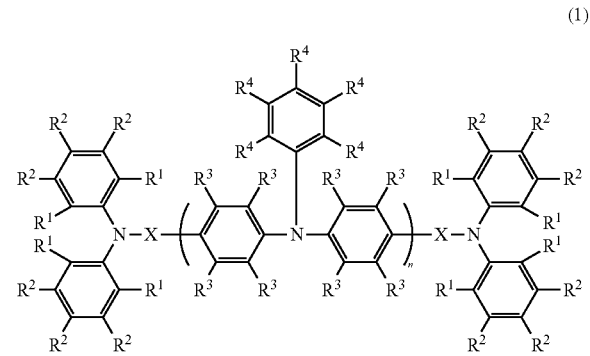

(1)

wherein $R^1$ to $R^4$ each independently represent a substituent selected from a linear, branched or cyclic monovalent hydrocarbon group having 1 to 20 carbon atoms, alkoxy group having 1 to 20 carbon atoms, aryloxy group having 6 to 20 carbon atoms, halogen atom, hydrogen atom, amino group, cyano group, amine-containing group, and siloxane-containing group; with the proviso that when an amine-containing group as the substituent is not included, at least one of $R^1$ to $R^4$ is a siloxane-containing group represented by $S_x$-A-, and that when an amine-containing group as the substituent is included, at least one of $R^1$ to $R^4$ and a substituent of the amine-containing group is a siloxane-containing group represented by $S_x$-A-; a method of producing the same; and a fluorescent resin composition containing the same.

15 Claims, No Drawings

FLUORESCENT COMPOUND, METHOD FOR PRODUCING THE SAME, AND FLUORESCENT RESIN COMPOSITION

RELATED APPLICATION

This application claims priority from Japanese Patent Application No. 2013-029045, filed Feb. 18, 2013, the disclosure of which is incorporated by reference herein in its entirety.

FIELD AND BACKGROUND OF THE INVENTION

The present invention relates to a novel fluorescent compound, to a method for producing the same, and to a fluorescent resin composition.

Organic compounds having a fluorescent chromophore (referred to as "fluorescent compounds", hereinafter) are used as fluorescent ink and pigment in colorants for paper, fibers, resins and the like because they are less expensive than fluorescent inorganic compounds.

The colorants are generally classified into two categories, dyes and pigments. The pigment is an agglomerate of molecules having a chromophore and has a large particle size. In contrast, the dye is a chromophore-containing molecule dissolvable in media such as solvents and resins. Generally, materials colored with pigments are inferior in transparency, brightness and color saturation to materials colored with dyes because the colorants of the pigments have a larger particle size.

Generally, fluorescent compounds are often used as pigments except for fluorescent tags in which a chemical reaction takes place between molecules. One reason for this is that pigments can enhance light resistance because of their generally high light resistance. Another reason is that dyes have low solubility in low polar media.

For the above-described reasons, when resins are colored with fluorescent compounds, resins with relatively high polarity such as acrylic resins and polyester resins can also be colored with dyes. In contrast, in the case of resins with low polarity such as polyolefin resins and silicone resins, pigments are inevitably used because of the low solubility of dyes. In the case of coloring with pigments, the pigments must be finely ground to a size smaller than the wavelength of light and be uniformly dispersed in the resin in order to obtain transparent resin compositions. However, this process requires a large amount of energy and time.

As a method for enhancing compatibility between a resin with low polarity and a fluorescent compound, a method wherein a fluorescent compound is bonded to a resin is proposed. For example, Japanese Patent Laid-Open No. 2007-169535 describes a silicone resin obtained by bonding a fluorescent compound to an amino silicone resin.

A large number of compounds used as fluorescent compounds are known. For example, triarylamine derivatives, which can provide light emission of high luminance and high luminescence efficiency, are useful as luminescent materials for organic electroluminescent elements (Japanese Patent Laid-Open No. 58-65440 and Japanese Patent No. 3412348). However, compounds disclosed in Japanese Patent Laid-Open No. 58-65440 and Japanese Patent No. 3412348 have poor solubility in organic solvents and poor compatibility with resins. Thus, Japanese Patent No. 3897879 presents a compound produced by modifying a triarylamine derivative with an alkoxysilyl group to enhance its solubility in organic solvents.

Additionally, Japanese Patent Laid-Open No. 2007-63273 refers to a compound produced by coupling two molecules of triarylamine using a siloxanyl group as a spacer to enhance its solubility in organic solvents.

SUMMARY OF THE INVENTION

However, there are needs to further develop the above-described conventional techniques. For example, the method disclosed in Japanese Patent Laid-Open No. 2007-169535 is not preferable because the method has difficulty in completely removing the unreacted fluorescent compound, which aggregates and deposits during storage and use, leading to changes in appearance and optical properties. Additionally, the resin, which is a polymer, has a molecular weight distribution and the chemical structure of each molecule is heterogeneous. Therefore, it is difficult to homogeneously distribute the fluorescent compound within the resin. Furthermore, when a plurality of fluorescent substituents are close to each other within the molecule, excimer emission may change the color tone.

The method disclosed in Japanese Patent No. 3897879, which is an improvement of Japanese Patent Laid-Open No. 58-65440 and Japanese Patent No. 3412348, has a problem of poor stability during handling and storage because the alkoxysilyl group is reactive and subject to hydrolysis and dehydrative condensation.

The method disclosed in Japanese Patent Laid-Open No. 2007-63273 improves the solubility in organic solvents. But it scarcely improves the solubility in low polar solvents and resins such as aliphatic hydrocarbons and silicone resins, and it is difficult to use the compounds in these solvents or resins as dye or fluorescent materials.

The present invention, which has been created in view of the above-described situation, has an object to provide a fluorescent compound that has an excellent solubility in organic solvents and an excellent compatibility with resins or prepolymers and monomers, especially silicone resins, and that can be incorporated into a resin composition in a simple way, a fluorescent resin composition containing the same, and a method of producing the same.

That is, the present invention provides a fluorescent compound represented by the following general formula (1):

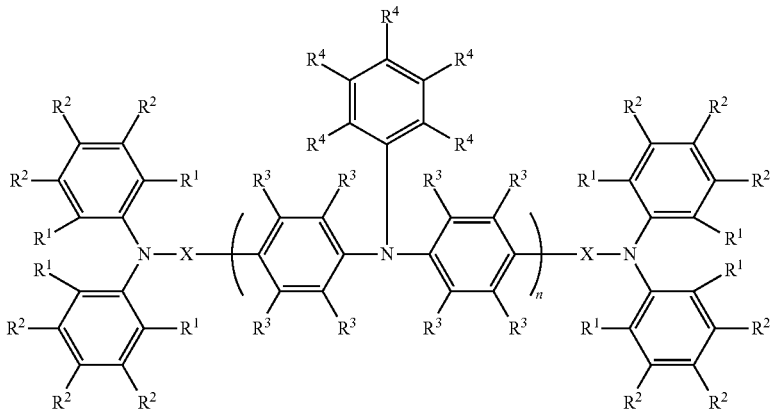

(1)

wherein $R^1$ to $R^4$ each independently represent a substituent selected from a linear, branched or cyclic monovalent hydrocarbon group having 1 to 20 carbon atoms, alkoxy group having 1 to 20 carbon atoms, aryloxy group having 6 to 20 carbon atoms, halogen atom, hydrogen atom, amino group, cyano group, amine-containing group represented by the following general formula (2), and siloxane-containing group represented by the following general formula (3); or the carbon atoms at the ortho position of the nitrogen atom bonded to X directly bonded to each other to form a carbazole ring structure, resulting in that $R^1$ is not present; with the proviso that when an amine-containing group represented by the general formula (2) as the substituent is not included, at least one of $R^1$ to $R^4$ is a siloxane-containing group represented by the following general formula (3), and that when an amine-containing group represented by the general formula (2) as the substituent is included, at least one of $R^1$ to $R^6$ is a siloxane-containing group represented by the following general formula (3);

each of X may be identical or different, represents a single bond, or a linear, branched or cyclic divalent hydrocarbon group having 1 to 20 carbon atoms, and some of the carbon atoms may be substituted with a heteroatom; and n is an integer of 0 to 5,

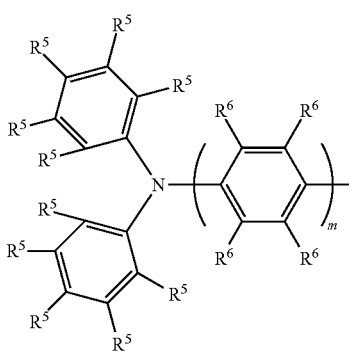

(2)

wherein $R^5$ and $R^6$ each independently represent a substituent selected from a linear, branched or cyclic monovalent hydrocarbon group having 1 to 20 carbon atoms, alkoxy group having 1 to 20 carbon atoms, aryloxy group having 6 to 20 carbon atoms, halogen atom, hydrogen atom, amino group, and siloxane-containing group represented by the following general formula (3); and m is 0 or 1;

$$S_x\text{-A-} \qquad (3)$$

wherein $S_x$ represents a linear, branched or cyclic organosiloxanyl group having 2 to 10 silicon atoms and a monovalent hydrocarbon group having 1 to 20 carbon atoms bonded to at least one of the silicon atoms; and A represents a single bond or a linear, branched or cyclic divalent hydrocarbon group having 1 to 20 carbon atoms which may contain at least one of —O—, —S— or —NR°—, or a combination thereof, with the proviso that heteroatoms of oxygen, sulfur and nitrogen are not adjacent to each other except the case where A is a cyclic divalent hydrocarbon group, and R° is a monovalent hydrocarbon group having 1 to 20 carbon atoms.

A preferable embodiment includes a fluorescent compound, wherein, in the general formula (1), n is 1, 3, or 5, and at least one of $R^4$ is a siloxane-containing group represented by the general formula (3).

Another preferable embodiment includes a fluorescent compound, wherein, in the general formula (1), at least one of $R^2$ is an amine-containing group represented by the general formula (2), and at least one of $R^5$ is a siloxane-containing group represented by the general formula (3).

Still another preferable embodiment includes a fluorescent compound, wherein, in the general formula (1), n is 0, and at least one of $R^2$ is a siloxane-containing group represented by the general formula (3).

According to another embodiment, the present invention is a fluorescent resin composition comprising any of the above-described fluorescent compounds and a resin.

In a preferable embodiment, the resin is a silicone resin.

According to another aspect, the present invention is a method for producing a fluorescent compound of the general formula (1) wherein n is 1, 3, or 5, and at least one of $R^4$ is a siloxane-containing group represented by the general formula (3), comprising a step of reacting an amine compound represented by the following general formula (4) with an aromatic halogen compound represented by the following general formula (5) in the presence of a transition metal catalyst:

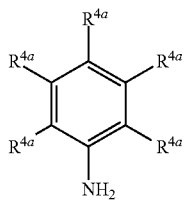
(4)

wherein $R^{4a}$ is identical to $R^4$ in the general formula (1);

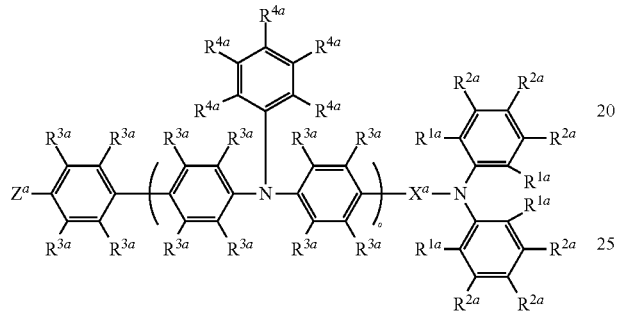
(5)

wherein, $R^{1a}$ to $R^{4a}$ are identical to $R^1$ to $R^4$ in the general formula (1), respectively;

$Z^a$ is a halogen atom;

$X^a$ is identical to X in the general formula (1); and o represents an integer of 0 to 2, and satisfies, together with n in the general formula (1), o=(n−1)/2.

According to another aspect, the present invention is a method for producing a fluorescent compound of the general formula (1) wherein at least one of $R^2$ is an amine-containing group represented by the general formula (2), and at least one of $R^5$ is a siloxane-containing group represented by the general formula (3), comprising a step of reacting an amine compound represented by the following general formula (6) with an aromatic halogen compound represented by the following general formula (7) in the presence of a transition metal catalyst:

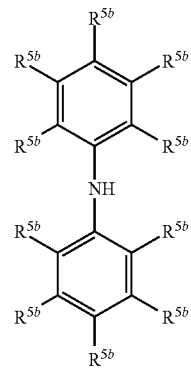
(6)

wherein $R^{5b}$ is identical to $R^5$ in the general formula (2);

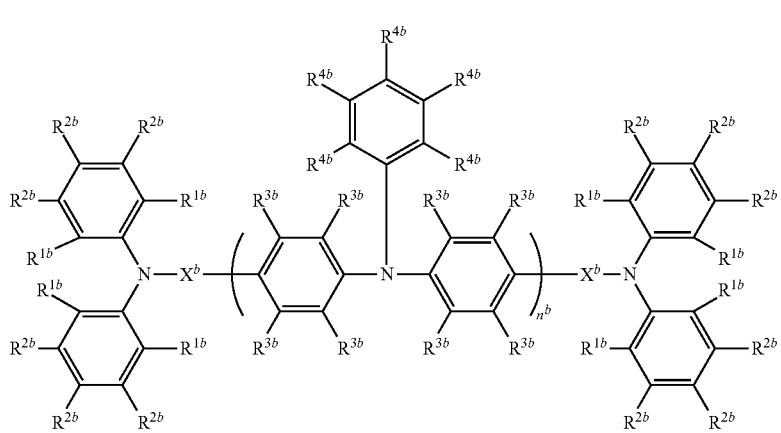
(7)

wherein $R^{1b}$ to $R^{4b}$ are identical to $R^1$ to $R^4$ in the general formula (1), respectively;

$X^b$ is identical to X in the general formula (1); and $n^b$ is identical to n in the general formula (1);

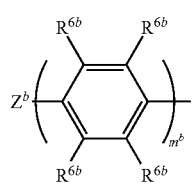
(8)

wherein $R^{6b}$ is identical to $R^6$ in the general formula (2); $m^b$ is identical to m in the general formula (2); and $Z^b$ is a halogen atom;

with the proviso that at least one of $R^{2b}$ represents a substituent represented by the general formula (8).

According to still another aspect, the present invention is a method for producing a fluorescent compound of the general formula (1) wherein n is 0, and at least one of $R^2$ is a siloxane-containing group represented by the general formula (3), comprising a step of reacting an amine compound represented by the following general formula (10) with an aromatic halogen compound represented by the following general formula (9) in the presence of a transition metal catalyst:

$$Z^c\text{—}X^c\text{—}X^c\text{—}Z^c \quad (9)$$

wherein, $X^c$ is identical to X in the general formula (1); and $Z^c$ is a halogen atom;

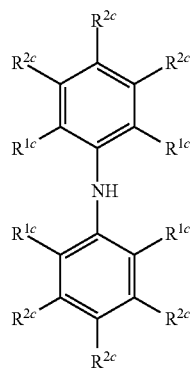

(10)

wherein $R^{1c}$ and $R^{2c}$ are identical to $R^1$ and $R^2$ in the general formula (1), respectively.

The fluorescent compound according to the present invention has an excellent solubility in organic solvents and an excellent compatibility with low polar resins, and has sufficient fluorescent properties as a fluorescent compound. Additionally, a fluorescent resin composition can be produced in a simple way using the fluorescent compound of the present invention. Furthermore, the fluorescent resin composition according to the present invention is excellent in transparency, brightness and color saturation, and can be preferably used particularly in applications such as fluorescent ink, wavelength converting materials, and dye lasers.

DETAILED DESCRIPTION OF THE PREFERRED EMBODIMENT

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

According to one embodiment, the present invention is a fluorescent compound. The fluorescent compound according to the present embodiment is represented by the above-described general formula (1).

In the general formula (1), $R^1$ to $R^4$ may be identical or different, and represent a substituent selected from a linear, branched or cyclic monovalent hydrocarbon group having 1 to 20 carbon atoms, preferably 1 to 12 carbon atoms; an alkoxy group having 1 to 20 carbon atoms, preferably 1 to 12 carbon atoms; an aryloxy group having 6 to 20 carbon atoms, preferably 6 to 12 carbon atoms; a halogen atom, hydrogen atom, amino group, cyano group, amine-containing group represented by the above-described general formula (2), and siloxane-containing group represented by the above-described general formula (3); or the carbons at the ortho position of the nitrogen atom bonded to X directly bond to each other to form a carbazole ring structure, resulting that $R^1$ is not present.

When an amine-containing group represented by the general formula (2) as the substituent is not included, at least one of $R^1$ to $R^4$ is a siloxane-containing group represented by the above-described general formula (3). In contrast, in the general formula (1), when an amine-containing group represented by the above-described general formula (2) as the substituent is included, at least one of $R^1$ to $R^6$ is a siloxane-containing group represented by the above-described general formula (3).

Specific examples of the above-described monovalent hydrocarbon group that may constitute $R^1$ to $R^4$ include linear saturated hydrocarbon groups, such as a methyl group, ethyl group, propyl group, butyl group, hexyl group, heptyl group, octyl group, nonyl group, decyl group, undecyl group, dodecyl group, tetradecyl group, hexadecyl group, octadecyl group, and icosyl group, branched saturated hydrocarbon groups, such as an isopropyl group, isobutyl group, sec-butyl group, tert-butyl group, pentyl group, cyclopentyl group, isopentyl group, 2-pentyl group, 3-pentyl group, and tert-pentyl group; cyclic saturated hydrocarbon groups, such as a cyclohexyl group and cyclopentyl group; unsaturated hydrocarbon groups, such as alkenyl groups, such as a vinyl group, allyl group, propenyl group, 1-methyl propenyl group, butenyl group, pentenyl group, hexenyl group, heptenyl group, octenyl group, nonenyl group, decenyl group, undecenyl group, and octadecenyl group, and alkynyl groups, such as an ethynyl group and propynyl group; aryl groups, such as a phenyl group, naphthyl group, benzyl group, phenethyl group, phenylpropyl group, 2-methylphenyl group, 3-methylphenyl group, 4-methylphenyl group, 2,4-dimethyl phenyl group, 3,5-dimethylphenyl group, 3,5-di-tert-butyl phenyl group, and biphenyl group, and aromatic hydrocarbon groups, such as an aralkyl group.

Of these, particularly preferred are a methyl group, ethyl group, propyl group, isopropyl group, butyl group, isobutyl group, sec-butyl group, tert-butyl group, pentyl group, hexyl group, heptyl group, octyl group, nonyl group, decyl group, undecyl group, dodecyl group, vinyl group, allyl group, and phenyl group.

Examples of the above-described alkoxy groups include a methoxy group, ethoxy group, butoxy group, tert-butoxy group, and hexyloxy group.

Examples of the above-described aryloxy groups include a phenoxy group, p-methylphenoxy group, and naphthoxy group.

Examples of the above-described halogen atoms include fluorine, chlorine, bromine, and iodine.

Examples of the above-described amino groups include a dimethylamino group and diethylamino group.

In the above-described general formula (2), $R^5$ and $R^6$ may be identical or different, and represent a substituent selected from a linear, branched or cyclic monovalent hydrocarbon group having 1 to 20 carbon atoms, preferably 1 to 12 carbon atoms; an alkoxy group having 1 to 20 carbon atoms, preferably 1 to 12 carbon atoms; an aryloxy group having 6 to 20 carbon atoms, preferably 6 to 12 carbon atoms; a halogen atom, hydrogen atom, amino group, and siloxane-containing group represented by the above-described general formula (3). m is 0 or 1.

Examples of the monovalent hydrocarbon group, alkoxy group, aryloxy group, halogen atom, and amino group that may constitute $R^5$ and $R^6$ are the same as those described for $R^1$ to $R^4$ in the general formula (1).

In the above-described general formula (3), $S_x$ represents a linear, branched or cyclic organosiloxanyl group which has 2 to 10 silicon atoms, preferably 2 to 8 silicon atoms, and more preferably 2 to 6 silicon atoms from a viewpoint of heat resistance, and also has a monovalent hydrocarbon group having 1 to 20 carbon atoms, preferably 1 to 10 carbon atoms, and more preferably 1 to 6 carbon atoms bonded to at least one of the silicon atoms. A larger number of silicon atoms increases the solubility in organic solvents, but may decrease the heat resistance.

Example of the monovalent hydrocarbon groups to be bonded to a silicon atom include alkyl groups, such as a methyl group, ethyl group, propyl group, isopropyl group, butyl group, sec-butyl group, and tert-butyl group; cycloalkyl groups, such as a cyclohexyl group; aryl groups, such as a phenyl group, tolyl group, and naphthyl group; alkenyl groups, such as a vinyl group, allyl group, propenyl group, and butenyl group; and aralkyl groups, such as a benzyl group and phenethyl group. The number of the monovalent hydrocarbon groups to be bonded to silicon atoms in $S_x$ is, for example, 1 to 10, preferably 1 to 8, and more preferably 1 to 6.

Specific examples of $S_x$ include linear organosiloxanyl groups, such as a pentamethyldisiloxan-1-yl group, 3,3,3-triethyl-1,1-dimethyldisiloxan-1-yl group, pentaethyldisiloxan-1-yl group, 3-vinyl-1,1,3,3-tetramethyldisiloxan-1-yl group, 3-benzyl-1,1,3,3-tetramethyldisiloxan-1-yl group, 3-tert-butyl-1,1,3,3-tetramethyldisiloxan-1-yl group, 3,3,3-triisopropyl-1,1-dimethyldisiloxan-1-yl group, 3-phenyl-1,1,3,3-tetramethyldisiloxan-1-yl group, 1,1-diphenyl-3,3,3-trimethyldisiloxan-1-yl group, 3,3-diphenyl-1,1,3-trimethyldisiloxan-1-yl group, 3,3,3-triphenyl-1,1-dimethyldisiloxan-1-yl group, 3-methyl-1,1,3,3-tetraphenyldisiloxan-1-yl group, pentaphenyldisiloxan-1-yl group, 1-cyclohexyl-1,3,3,3-tetramethyldisiloxan-1-yl group, heptamethyltrisiloxan-1-yl group, 5-phenyl-1,1,3,3,5,5-hexamethyltrisiloxan-1-yl group, 5,5-diphenyl-1,1,3,3,5-pentamethyltrisiloxan-1-yl group, 5,5,5-triphenyl-1,1,3,3-tetramethyltrisiloxan-1-yl group, 3,3,5-triphenyl-1,1,5,5-tetramethyltrisiloxan-1-yl group, heptaphenyltrisiloxan-1-yl group, nonamethyltetrasiloxan-1-yl group, 7,7,7-triphenyl-1,1,3,3,5,5-hexamethyltetrasiloxan-1-yl group, 5,5,7,7,7-pentaphenyl-1,1,3,3-tetramethyltetrasiloxan-1-yl group, 3,3,5,5,7,7,7-heptaphenyl-1,1-dimethyltetrasiloxan-1-yl group, nonaphenyltetrasiloxan-1-yl group, undecamethylpentasiloxan-1-yl group, 9,9,9-triphenyl-1,1,3,3,5,5,7,7-octamethylpentasiloxan-1-yl group, 7,7,9,9,9-pentaphenyl-1,1,3,3,5,5-hexamethylpentasiloxan-1-yl group, 5,5,7,7,9,9,9-heptaphenyl-1,1,3,3-tetramethylpentasiloxan-1-yl group, 3,3,5,5,7,7,9,9,9-decaphenyl-1,1-dimethylpentasiloxan-1-yl group, undecaphenylpentasiloxan-1-yl group, tridecamethylhexasiloxan-1-yl group, pentadecamethylheptasiloxan-1-yl group, heptadecamethyloctasiloxan-1-yl group, nonadecamethylnonasiloxan-1-yl group, and henicosamethyldecasiloxan-1-yl group; branched organosiloxanyl groups, such as a 1-trimethylsiloxy-1,3,3,3-tetramethyldisiloxan-1-yl group, 1-phenyldimethylsiloxy-1,3,3,3-tetramethyldisiloxan-1-yl group, 1-phenyldimethylsiloxy-3-phenyl-1,3,3-tetramethyldisiloxan-1-yl group, 1-phenyldimethylsiloxy-1,3-diphenyl-3,3-dimethyldisiloxan-1-yl group, 1,1,5,5-tetraphenyl-1,3,5-trimethyltrisiloxan-3-yl group, 1,1,1,5,5,5-hexaphenyl-3-methyltrisiloxan-3-yl group, 1-trimethylsiloxy-1,3,3,5,5,5-hexamethyltrisiloxan-1-yl group, 1-pentamethyldisiloxanyloxy-1,3,3,5,5,5-hexamethyltrisiloxan-1-yl group, 1-trimethylsiloxy-1,3,3,5,5,7,7,7-octamethyltetrasiloxan-1-yl group, 1,1-bis(trimethylsiloxy)-3,3,3-trimethyldisiloxan-1-yl group, 1-triphenylsiloxy-1,3,3,3-tetraphenyldisiloxan-1-yl group, 1-triphenylsiloxy-1,3,3,5,5,5-hexaphenyltrisiloxan-1-yl group, 1-pentaphenyldisiloxanyloxy-1,3,3,5,5,5-hexaphenyltrisiloxan-1-yl group, 1-triphenylsiloxy-3,5,5,7,7,9,9,9-octaphenyltetrasiloxan-1-yl group, and 1,1-bis(triphenylsiloxy)-3,3,3-triphenyldisiloxan-1-yl group; cyclic organosiloxanyl groups, such as a 1,3,3,5,5,7,7-heptamethylcyclotetrasiloxan-1-yl group, 1,3,5,7-tetramethyl-3,5,7-trivinylcyclotetrasiloxan-1-yl group, 1,3,3,5,5,7,7-heptaphenylcyclotetrasiloxan-1-yl group, and 1,3,5,7-tetraphenyl-3,5,7-trivinylcyclotetrasiloxan-1-yl group.

Of these, particularly preferred are a pentamethyldisiloxan-1-yl group, heptamethyltrisiloxan-1-yl group, nonamethyltetrasiloxan-1-yl group, undecamethylpentasiloxan-1-yl group, 1-trimethylsiloxy-1,3,3,3-tetramethyldisiloxan-1-yl group, 1,3,3,5,5,7,7-heptamethylcyclotetrasoxan-1-yl group, pentaphenyldisiloxan-1-yl group, heptaphenyltrisiloxan-1-yl group, nonaphenyltetrasiloxan-1-yl group, undecaphenylpentasiloxan-1-yl group, 1-triphenylsiloxy-1,3,3,3-tetraphenyldisiloxan-1-yl group, and 1,3,3,5,5,7,7-heptaphenylcyclotetrasiloxan-1-yl group as $S_x$, from the viewpoint of ease of synthesis.

In the above-described general formula (3), A represents a single bond or a linear, branched or cyclic divalent hydrocarbon group having 1 to 20 carbon atoms, preferably 1 to 12 carbon atoms that may contain at least one —O—, —S— or —NR⁰— or a combination thereof, with the proviso that heteroatoms of oxygen, sulfur and nitrogen are not adjacent to each other except the case where A is a cyclic divalent hydrocarbon group. $R^0$ is a monovalent hydrocarbon group having 1 to 20 carbon atoms.

$R^0$ is a monovalent hydrocarbon group having 1 to 20 carbon atoms, preferably 1 to 12 carbon atoms, and specifically includes linear saturated hydrocarbon groups, such as a methyl group, ethyl group, propyl group, butyl group, hexyl group, pentyl group, octyl group, decyl group, dodecyl group, tetradecyl group, hexadecyl group, octadecyl group, and icosyl group; branched saturated hydrocarbon groups, such as an isopropyl group, isobutyl group, sec-butyl group, tert-butyl group, isopentyl group; 2-pentyl group, 3-pentyl group, and tert-pentyl group; saturated hydrocarbon groups, such as cyclic alkyl groups, such as a cyclohexyl group and cyclopentyl group; unsaturated hydrocarbon groups, such as alkenyl groups, such as a vinyl group, allyl group, propenyl group, 1-methylpropenyl group, butenyl group, pentenyl group, hexenyl group, heptenyl group, octenyl group, nonenyl group, decenyl group, undecenyl group, and octadecenyl group; and alkynyl groups; and aromatic hydrocarbon groups, such as aryl groups, such as a phenyl group, naphthyl group, benzyl group, phenethyl group, phenylpropyl group, 2-methylphenyl group, 3-methylphenyl group, 4-methylphenyl group, 2,4-dimethylphenyl group, 3,5-dimethylphenyl group, and 3,5-di-tert-butylphenyl group, and aralkyl groups. Of these, particularly preferred are a methyl group, ethyl group, propyl group, isopropyl group, butyl group, isobutyl group, sec-butyl group, tert-butyl group, pentyl group, hexyl group, octyl group, decyl group, dodecyl group, vinyl group, allyl group, and phenyl group. The general formula (3) may include a plurality of $R^6$ groups, which may be identical or different.

Specific examples of the substituent represented by A include a single bond; linear, branched or cyclic aliphatic divalent hydrocarbon groups, such as a methylene group, 1,2-ethanediyl group, 1,1-ethanediyl group, 1,2-ethenediyl group, 1,1-ethenediyl group, 1,3-propanediyl group, 1,2-propanediyl group, 2-methyl-1,3-propanediyl group, 1,3-butanediyl group, 1,4-butanediyl group, 1,5-pentanediyl group, 1,6-hexanediyl group, 1,4-cyclohexanediyl group, 1,7-heptanediyl group, 1,8-octanediyl group, 1,9-nonanediyl group, 1,10-decanediyl group, 1,11-undecanediyl group, 1,12-dodecanediyl group, 1,13-tridecanediyl group, 1,14-tetradecanediyl group, 1,15-pentadecanediyl group, 1,16-hexadecanediyl group, 1,17-heptadecanediyl group, 1,18-octadecanediyl group, 1,19-nonadecanediyl group, and 1,20-icosandiyl group; aromatic divalent hydrocarbon groups, such as a 1,3-benzenediyl group, 1,4-benzenediyl group, 2-methyl-1,4-benzenediyl group, 3-methyl-1,4-benzenediyl group, 2,5-dimethyl-1,4-benzenediyl group, 1,8-naphthalenediyl group, 2,7-naphthalenediyl group, 1,4-anthracenediyl group, 1,5-anthracenediyl group, 2,6-anthracenediyl group, 9,10-anthracenediyl group, 1,6-pyrenediyl group, 1,8-pyrenediyl group, 2,7-pyrenediyl group, 4,9-pyrenediyl group, 4-ethylbenzene-1,2'-diyl group, and 4-propylbenzene-1,3'-diyl group; heteroatom-containing divalent hydrocarbon groups, such as 2-oxa-1,3-propanediyl group, 3-oxa-1,5-pentanediyl group, 3-oxa-2-methyl-1,5-pentanediyl group, 3-oxa-1,6-hexanediyl group, 3-oxa-2-methyl-1,5-hexanediyl group, 3-oxa-2-methyl-1,6-hexanediyl group, 3,6-dioxa-1,8-octanediyl group, 3,7-dioxa-1,9-nonanediyl group, 3-methyl-3-aza-1,5-pentanediyl group, 3-methyl-3-aza-1,6-hexanediyl group, 3-phenyl-3-aza-1,6-hexanediyl group, 3-methyl-3-aza-7-oxa-1,9-nonanediyl group, 3-thia-1,5-pentanediyl group, 3,6-dithia-1,8-octanediyl group, 2,5-furandiyl group, 2,5-thiophenediyl group, 1,2,4-oxadiazol-3,5-diyl group, 1,3,4-oxadiazol-2,5-diyl group, 1,2,4-thiadiazol-3,5-diyl group, and 1,3,4-thiadiazol-2,5-diyl group.

Of these, particularly preferred are a single bond, methylene group, 1,2-ethanediyl group, 1,3-propanediyl group, 2-methyl-1,3-propanediyl group, 1,4-butanediyl group, 1,5-pentanediyl group, 1,6-hexanediyl group, 1,7-heptanediyl group, 1,8-octanediyl group, 1,9-nonanediyl group, 1,10-decanediyl group, and 1,11-undecanediyl group as the substituent represented by A, from a viewpoint of being able to impart higher solubility.

In the general formula (3), any combination of $S_x$ and A is possible. In the case where $S_x$ is an undecamethylpentasiloxan-1-yl group, the specific examples of the siloxane-containing group represented by the general formula (3) include siloxanyl groups, such as an undecamethylpentasiloxan-1-yl group; substituted hydrocarbon groups, such as an undecamethylpentasiloxan-1-ylmethyl group, 2-(undecamethylpentasiloxan-1-yl)ethyl group, 1-(undecamethylpentasiloxan-1-yl)ethyl group, 2-(undecamethylpentasiloxan-1-yl)ethenyl group, 3-(undecamethylpentasiloxan-1-yl)propyl group, 2-methyl-3-(undecamethylpentasiloxan-1-yl)propyl group, 4-(undecamethylpentasiloxan-1-yl)butyl group, 5-(undecamethylpentasiloxan-1-yl)pentyl group, 6-(undecamethylpentasiloxan-1-yl)hexyl group, 7-(undecamethylpentasiloxan-1-yl)heptyl group, 8-(undecamethylpentasiloxan-1-yl)octyl group, 9-(undecamethylpentasiloxan-1-yl)nonyl group, 10-(undecamethylpentasiloxan-1-yl)decyl group, 11-(undecamethylpentasiloxan-1-yl)undecyl group, 12-(undecamethylpentasiloxan-1-yl)dodecyl group, 14-(undecamethylpentasiloxan-1-yl)tetradecyl group, 16-(undecamethylpentasiloxan-1-yl)hexadecyl group, 18-(undecamethylpentasiloxan-1-yl)octadecyl group, 20-(undecamethylpentasiloxan-1-yl)icosyl group, 4-(undecamethylpentasiloxan-1-yl)phenyl group, 3-(undecamethylpentasiloxan-1-yl)phenyl group, 4-[2-(undecamethylpentasiloxan-1-yl)ethyl]phenyl group, 4-[3-(undecamethylpentasiloxan-1-yl)propyl]phenyl group, 4-[2-(undecamethylpentasiloxan-1-yl)propyl]phenyl group, 2-{2-(undecamethylpentasiloxan-1-yl)ethoxy}ethyl group, 3-{2-(undecamethylpentasiloxan-1-yl)ethoxy}propyl group, 2-[3-(undecamethylpentasiloxan-1-yl)propoxy]ethyl group, 2-{3-(undecamethylpentasiloxan-1-yl)propoxy}propyl group, 2-{2-{3-(undecamethylpentasiloxan-1-yl)propoxy}ethoxy}ethyl group, 2-{2-{3-(undecamethylpentasiloxan-1-yl)propoxy}propoxy}ethyl group, and 2-{2-{3-(undecamethylpentasiloxan-1-yl)propoxy}propoxy}propyl group; substituted organoxy groups, such as an (undecamethylpentasiloxan-1-yl)methoxy group, 2-(undecamethylpentasiloxan-1-yl)ethoxy group, 3-(undecamethylpentasiloxan-1-yl)propoxy group, 2-methyl-3-(undecamethylpentasiloxan-1-yl)propoxy group, 3-(undecamethylpentasiloxan-1-yl)butoxy group, 4-(undecamethylpentasiloxan-1-yl)butoxy group, 4-(undecamethylpentasiloxan-1-yl)phenoxy group, 2-{2-(undecamethylpentasiloxan-1-yl)ethoxy}ethoxy group, 3-{2-(undecamethylpentasiloxan-1-yl)ethoxy}propoxy group, 2-{3-(undecamethylpentasiloxan-1-yl)propoxy}ethoxy group, 2-{3-(undecamethylpentasiloxan-1-yl)propoxy}propoxy group, 2-{2-{3-(undecamethylpentasiloxan-1-yl)propoxy}ethoxy}ethoxy group, 2-{2-{3-(undecamethylpentasiloxan-1-yl)propoxy}propoxy}ethoxy group, 2-{2-{3-(undecamethylpentasiloxan-1-yl)propoxy}propoxy}propoxy group, 2-[N-methyl-N-{3-(undecamethylpentasiloxan-1-yl)propyl}amino]ethoxy group, 2-[N-methyl-N-{3-(undecamethylpentasiloxan-1-yl)propyl}amino]ethoxy group, 1-methyl-2-[N-methyl-N-{3-(undecamethylpentasiloxan-1-yl)propyl}amino]ethoxy group, and 2-[2-(undecamethylpentasiloxan-1-yl)ethylsulfanyl]ethoxy group; substituted organoxycarbonyl groups, such as an (undecamethylpentasiloxan-1-yl)methoxycarbonyl group, 2-(undecamethylpentasiloxan-1-yl)ethoxycarbonyl group, 3-(undecamethylpentasiloxan-1-yl)propoxycarbonyl group, 2-methyl-3-(undecamethylpentasiloxan-1-yl)propoxycarbonyl group, 3-(undecamethylpentasiloxan-1-yl)butoxycarbonyl group, 4-(undecamethylpentasiloxan-1-yl)phenoxycarbonyl group, 2-[2-(undecamethylpentasiloxan-1-yl)ethoxy]ethoxycarbonyl group, 3-{2-(undecamethylpentasiloxan-1-yl)ethoxy}propoxycarbonyl group, 2-{3-(undecamethylpentasiloxan-1-yl)propoxy}ethoxycarbonyl group, 2-{3-(undecamethylpentasiloxan-1-yl)propoxy}propoxycarbonyl group, 2-{2-{3-(undecamethylpentasiloxan-1-yl)propoxy}ethoxy}ethoxycarbonyl group, 2-{2-{3-(undecamethylpentasiloxan-1-yl)propoxy}propoxy}ethoxycarbonyl group, 2-{2-{3-(undecamethylpentasiloxan-1-yl)propoxy}propoxy}propoxycarbonyl group, 2-[N-methyl-N-{3-(undecamethylpentasiloxan-1-yl)propyl}amino]ethoxycarbonyl group, 2-[N-methyl-N-{3-(undecamethylpentasiloxan-1-yl)propyl}amino]ethoxycarbonyl group, 1-methyl-2-[N-methyl-N-{3-(undecamethylpentasiloxan-1-yl)propyl}amino]ethoxycarbonyl group, and 2-{2-(undecamethylpentasiloxan-1-yl)

ethylsulfanyl}ethoxycarbonyl group; substituted acyloxy groups, such as an (undecamethylpentasiloxan-1-yl)acetoxy group, 3-(undecamethylpentasiloxan-1-yl)propionyloxy group, 2-methyl-3-(undecamethylpentasiloxan-1-yl)propionyloxy group, 5-(undecamethylpentasiloxan-1-yl)pentanoyloxy group, 6-(undecamethylpentasiloxan-1-yl)hexanoyloxy group, 11-(undecamethylpentasiloxan-1-yl)undecanoyloxy group, 4-(undecamethylpentasiloxan-1-yl)benzoyloxy group, {2-(undecamethylpentasiloxan-1-yl)ethoxy}acetyl group, 3-{2-(undecamethylpentasiloxan-1-yl)ethoxy}propionyloxy group, {3-(undecamethylpentasiloxan-1-yl)propoxy}acetoxy group, 3-{3-(undecamethylpentasiloxan-1-yl)propoxy}propionyloxy group, {2-{3-(undecamethylpentasiloxan-1-yl)propoxy}ethoxy}acetoxy group, {2-{3-(undecamethylpentasiloxan-1-yl)propoxy}propoxy}acetoxy group, 3-[N-methyl-N-{3-(undecamethylpentasiloxan-1-yl)propyl}amino]propionyloxy group, and 3-[N-methyl-N-{3-(undecamethylpentasiloxan-1-yl)propyl}amino]propionyloxy group.

The group represented by the general formula (3) is preferably a group obtained by combining the preferred example of the above-described $S_x$ and the preferred example of the above-described A. In particular, more preferred are a pentamethyldisiloxan-1-yl group, heptamethyltrisiloxan-1-yl group, nonamethyltetrasiloxan-1-yl group, undecamethylpentasiloxan-1-yl group, 1-trimethylsiloxy-1,3,3,3-tetramethyldisiloxan-1-yl group, 1,3,3,5,5,7,7-heptamethylcyclotetrasiloxan-1-yl group, pentaphenyldisiloxan-1-yl group, heptaphenyltrisiloxan-1-yl group, nonaphenyltetrasiloxan-1-yl group, undecaphenylpentasiloxan-1-yl group, 1-triphenylsiloxy-1,3,3,3-tetraphenyldisiloxan-1-yl group, 1,3,3,5,5,7,7-heptaphenylcyclotetrasiloxan-1-yl group, 3-(pentamethyldisiloxan-1-yl)propyl group, 3-(heptamethyltrisiloxan-1-yl)propyl group, 3-(nonamethyltetrasiloxan-1-yl)propyl group, 3-(undecamethylpentasiloxan-1-yl)propyl group, 3-(1-trimethylsiloxy-1,3,3,3-tetramethyldisiloxan-1-yl)propyl group, 3-(1,3,3,5,5,7,7-heptamethylcyclotetrasiloxan-1-yl)propyl group, 3-(pentaphenyldisiloxan-1-yl)propyl group, 3-(heptaphenyltrisiloxan-1-yl)propyl group, 3-(nonaphenyltetrasiloxan-1-yl)propyl group, 3-(undecaphenylpentasiloxan-1-yl)propyl group, 3-(1-triphenylsiloxy-1,3,3,3-tetraphenyldisiloxan-1-yl)propyl group, 3-(1,3,3,5,5,7,7-heptaphenylcyclotetrasiloxan-1-yl)propyl group, 4-(pentamethyldisiloxan-1-yl)butyl group, 4-(heptamethyltrisiloxan-1-yl)butyl group, 3-(nonamethyltetrasiloxan-1-yl)butyl group, 4-(undecamethylpentasiloxan-1-yl)butyl group, 4-(1-trimethylsiloxy-1,3,3,3-tetramethyldisiloxan-1-yl)butyl group, 4-(1,3,3,5,5,7,7-heptamethylcyclotetrasiloxan-1-yl)butyl group, 4-(pentaphenyldisiloxan-1-yl)butyl group, 4-(heptaphenyltrisiloxan-1-yl)butyl group, 3-(nonaphenyltetrasiloxan-1-yl)butyl group, 4-(undecaphenylpentasiloxan-1-yl)butyl group, 4-(1-triphenylsiloxy-1,3,3,3-tetraphenyldisiloxan-1-yl)butyl group, 4-(1,3,3,5,5,7,7-heptaphenylcyclotetrasiloxan-1-yl)butyl group, 5-(pentamethyldisiloxan-1-yl)pentyl group, 5-(heptamethyltrisiloxan-1-yl)pentyl group, 5-(nonamethyltetrasoxan-1-yl)pentyl group, 5-(undecamethylpentasiloxan-1-yl)pentyl group, 5-(1-trimethylsiloxy-1,3,3,3-tetramethyldisiloxan-1-yl)pentyl group, 5-(1,3,3,5,5,7,7-heptamethylcyclotetrasiloxan-1-yl)pentyl group, 5-(pentaphenyldisiloxan-1-yl)pentyl group, 5-(heptaphenyltrisiloxan-1-yl)pentyl group, 5-(nonaphenyltetrasiloxan-1-yl)pentyl group, 5-(undecaphenylpentasiloxan-1-yl)pentyl group, 5-(1-triphenylsiloxy-1,3,3,3-tetraphenyldisiloxan-1-yl)pentyl group, 5-(1,3,3,5,5,7,7-heptaphenylcyclotetrasiloxan-1-yl)pentyl group, 6-(pentamethyldisiloxan-1-yl)hexyl group, 6-(heptamethyltrisiloxan-1-yl)hexyl group, 6-(nonamethyltetrasiloxan-1-yl)hexyl group, 6-(undecamethylpentasiloxan-1-yl)hexyl group, 6-(1-trimethylsiloxy-1,3,3,3-tetramethyldisiloxan-1-yl)hexyl group, 6-(1,3,3,5,5,7,7-heptamethylcyclotetrasiloxan-1-yl)hexyl group, 6-(pentaphenyldisiloxan-1-yl)hexyl group, 6-(heptaphenyltrisiloxan-1-yl)hexyl group, 6-(nonaphenyltetrasiloxan-1-yl)hexyl group, 6-(undecaphenylpentasiloxan-1-yl)hexyl group, 6-(1-triphenylsiloxy-1,3,3,3-tetraphenyldisiloxan-1-yl)hexyl group, 6-(1,3,3,5,5,7,7-heptaphenylcyclotetrasiloxan-1-yl)hexyl group, 7-(pentamethyldisiloxan-1-yl)heptyl group, 7-(heptamethyltrisiloxan-1-yl)heptyl group, 7-(nonamethyltetrasiloxan-1-yl)heptyl group, 7-(undecamethylpentasiloxan-1-yl)heptyl group, 7-(1-trimethylsiloxy-1,3,3,3-tetramethyldisiloxan-1-yl)heptyl group, 7-(1,3,3,5,5,7,7-heptamethylcyclotetrasiloxan-1-yl)heptyl group, 7-(pentaphenyldisiloxan-1-yl)heptyl group, 7-(heptaphenyltrisiloxan-1-yl)heptyl group, 7-(nonaphenyltetrasiloxan-1-yl)heptyl group, 7-(undecaphenylpentasiloxan-1-yl)heptyl group, 7-(1-triphenylsiloxy-1,3,3,3-tetraphenyldisiloxan-1-yl)heptyl group, 7-(1,3,3,5,5,7,7-heptaphenylcyclotetrasiloxan-1-yl)heptyl group, 8-(pentamethyldisiloxan-1-yl)octyl group, 8-(heptamethyltrisiloxan-1-yl)octyl group, 8-(nonamethyltetrasiloxan-1-yl)octyl group, 8-(undecamethylpentasiloxan-1-yl)octyl group, 8-(1-trimethylsiloxy-1,3,3,3-tetramethyldisiloxan-1-yl)octyl group, 8-(1,3,3,5,5,7,7-heptamethylcyclotetrasiloxan-1-yl)octyl group, 8-(pentaphenyldisiloxan-1-yl)octyl group, 8-(heptaphenyltrisiloxan-1-yl)octyl group, 8-(nonaphenyltetrasiloxan-1-yl)octyl group, 8-(undecaphenylpentasiloxan-1-yl)octyl group, 8-(1-triphenylsiloxy-1,3,3,3-tetraphenyldisiloxan-1-yl)octyl group, 8-(1,3,3,5,5,7,7-heptaphenylcyclotetrasiloxan-1-yl)octyl group, 9-(pentamethyldisiloxan-1-yl)nonyl group, 9-(heptamethyltrisiloxan-1-yl)nonyl group, 9-(nonamethyltetrasiloxan-1-yl)nonyl group, 9-(undecamethylpentasiloxan-1-yl)nonyl group, 9-(1-trimethylsiloxy-1,3,3,3-tetramethyldisiloxan-1-yl)nonyl group, 9-(1,3,3,5,5,7,7-heptamethylcyclotetrasiloxan-1-yl)nonyl group, 9-(pentaphenyldisiloxan-1-yl)nonyl group, 9-(heptaphenyltrisiloxan-1-yl)nonyl group, 9-(nonaphenyltetrasiloxan-1-yl)nonyl group, 9-(undecaphenylpentasiloxan-1-yl)nonyl group, 9-(1-triphenylsiloxy-1,3,3,3-tetraphenyldisiloxan-1-yl)nonyl group, 9-(1,3,3,5,5,7,7-heptaphenylcyclotetrasiloxan-1-yl)nonyl group, 10-(pentamethyldisiloxan-1-yl)decyl group, 10-(heptamethyltrisiloxan-1-yl)decyl group, 10-(nonamethyltetrasiloxan-1-yl)decyl group, 10-(undecamethylpentasiloxan-1-yl)decyl group, 10-(1-trimethylsiloxy-1,3,3,3-tetramethyldisiloxan-1-yl)decyl group, 10-(1,3,3,5,5,7,7-heptamethylcyclotetrasiloxan-1-yl)decyl group, 10-(pentaphenyldisiloxan-1-yl)decyl group, 10-(heptaphenyltrisiloxan-1-yl)decyl group, 10-(nonaphenyltetrasiloxan-1-yl)decyl group, 10-(undecaphenylpentasiloxan-1-yl)decyl group, 10-(1-triphenylsiloxy-1,3,3,3-tetraphenyldisiloxan-1-yl)decyl group, 10-(1,3,3,5,5,7,7-heptaphenylcyclotetrasiloxan-1-yl)decyl group, 11-(pentamethyldisiloxan-1-yl)undecyl group, 11-(heptamethyltrisiloxan-1-yl)undecyl group, 11-(nonamethyltetrasiloxan-1-yl)undecyl group, 11-(undecamethylpentasiloxan-1-yl)undecyl group, 11-(1-trimethylsiloxy-1,3,3,3-tetramethyldisiloxan-1-yl)undecyl group, 11-(1,3,3,5,5,7,7-heptamethylcyclotetrasiloxan-1-yl)undecyl group, 11-(pentaphenyldisiloxan-1-yl)undecyl group, 11-(heptaphenyltrisiloxan1-yl)undecyl group, 11-(nonaphenyltetrasiloxan-1-yl)undecyl group, 11-(undecaphenylpentasiloxan-1-yl)undecyl group, 11-(1-triphenylsiloxy-1,3,3,3-tetraphenyldisiloxan-1-yl)undecyl group, and 11-(1,3,3,5,5,7,7-heptaphenylcyclotetrasiloxan-1-yl)undecyl group.

In the general formula (1), X may be identical or different, and represents a single bond, or a linear, branched or cyclic divalent hydrocarbon group having 1 to 20 carbon atoms. Some of the carbon atoms may be replaced by a heteroatom. In this case, the total number of heteroatoms and carbon atoms in the divalent hydrocarbon group is 1 to 20.

Specific examples of X include a single bond; linear, branched or cyclic aliphatic divalent hydrocarbon groups such as a methylene group, 1,2-ethanediyl group, 1,1-ethanediyl group, 1,2-ethenediyl group, 1,1-ethenediyl group, 1,3-propanediyl group, 1,2-propanediyl group, 2-methyl-1,3-propanediyl group, 1,3-butanediyl group, 1,4-butanediyl group, 1,5-pentanediyl group, 1,6-hexanediyl group, 1,4-cyclohexanediyl group, 1,7-heptanediyl group, 1,8-octanediyl group, 1,9-nonanediyl group, 1,10-decanediyl group, 1,11-undecanediyl group, 1,12-dodecanediyl group, 1,13-tridecanediyl group, 1,14-tetradecanediyl group, 1,15-pentadecanediyl group, 1,16-hexadecanediyl group, 1,17-heptadecanediyl group, 1,18-octadecanediyl group, 1,19-nonanedecanediyl group, and 1,20-icosandiyl group; aromatic divalent hydrocarbon groups such as 1,3-benzenediyl group, 1,4-benzenediyl group, 2-methyl-1,4-benzenediyl group, 3-methyl-1,4-benzenediyl group, 2,5-dimethyl-1,4-benzenediyl group, 1,8-naphthalenediyl group, 2,7-naphthalenediyl group, 1,4-anthracenediyl group, 1,5-anthracenediyl group, 2,6-anthracenediyl group, 9,10-anthracenediyl group, 1,6-pyrenediyl group, 1,8-pyrenediyl group, 2,7-pyrenediyl group, 4,9-pyrenediyl group, 4-ethylbenzene-1,2'-diyl group, and 4-propylbenzene-1,3'-diyl group; heteroatom-containing divalent hydrocarbon groups such as a 2-oxa-1,3-propanediyl group, 3-oxa-1,5-pentanediyl group, 3-oxa-2-methyl-1,5-pentanediyl group, 3-oxa-1,6-hexanediyl group, 3-oxa-2-methyl-1,5-hexanediyl group, 3-oxa-2-methyl-1,6-hexanediyl group, 3,6-dioxa-1,8-octanediyl group, 3,7-dioxa-1,9-nonanediyl group, 3-methyl-3-aza-1,5-pentanediyl group, 3-methyl-3-aza-1,6-hexanediyl group, 3-phenyl-3-aza-1,6-hexanediyl group, 3-methyl-3-aza-7-oxa-1,9-nonanediyl group, 3-thia-1,5-pentanediyl group, 3,6-dithia-1,8-octanediyl group, 2,5-furandiyl group, 2,5-thiophendiyl group, 1,2,4-oxadiazol-3,5-diyl group, 1,3,4-oxadiazol-2,5-diyl group, 1,2,4-thiadiazol-3,5-diyl group, and 1,3,4-thiadiazol-2,5-diyl group.

Of these, particularly preferred are a single bond, 1,3-benzenediyl group, 1,4-benzenediyl group, 2-methyl-1,4-benzenediyl group, 3-methyl-1,4-benzenediyl group, 2,5-dimethyl-1,4-benzenediyl group, 1,8-naphthalenediyl group, 2,7-naphthalenediyl group, 1,4-anthracenediyl group, 1,5-anthracenediyl group, 2,6-anthracenediyl group, and 9,10-anthracenediyl group as X, from a viewpoint of ease of synthesis.

The fluorescent compound of the present invention represented by the above-described general formula (1) is characterized by including a siloxane-containing group represented by the general formula (3). In this context, the siloxane moiety of the siloxane-containing group, of which structure is clearly specified, is not a siloxane mixture having a molecular weight distribution. Thus, the compound represented by the general formula (1) is not a mixture either but a single compound. In producing a composition by use of a fluorescent compound, the molar concentration of its fluorescent chromophore is an important factor that determines the fluorescent properties of the composition. Accordingly, the fluorescent compound represented by the general formula (1) is preferably a single compound in order to determine the molar concentration precisely.

The fluorescent compound according to the present invention represented by the above-described general formula (1) is desirably purified to high purity as much as possible, in order to allow the compound to fully exert its fluorescent properties. As described above, being a single compound, the fluorescent compound of the present invention represented by the general formula (1) can be purified to high purity. Examples of the purification method include recrystallization and crystallization, sublimation, washing with solvents, silica gel column chromatography, gel filtration chromatography, and preparative liquid chromatography, as with normal organic compounds. The purity of the fluorescent compound of the present invention is preferably 95% or more, more preferably 98% or more, and still more preferably 99% or more, in the case of liquid chromatography purification. If a large amount of impurities is included, the fluorescent compound represented by the general formula (1) itself may have reduced fluorescent properties. In producing a fluorescent resin composition using such a fluorescent compound, the fluorescent resin composition may become clouded, thereby reducing the fluorescent properties of the composition as well.

Purity determination with liquid chromatography is feasible under either of the normal phase or reverse phase condition. For the normal phase, Inertsil (R) Diol columns produced by GL Sciences Inc. are used, and for the reverse phase, XBridge (R) C18 columns produced by Waters Corporation are used, for example. For size exclusion chromatography, which is also an effective method, TSK-GEL SuperHZ2000 columns produced by TOSOH CORPORATION can be used, for example.

The method for producing the fluorescent compound according to the present invention represented by the above-described general formula (1) is now described. The fluorescent compound of the present invention, which is a triarylamine derivative, can be produced in various methods. Examples of the methods include a method comprising introducing a siloxane-containing group into a triarylamine derivative with no siloxane-containing group that has been produced by a known method. Alternatively, methods that include steps of: preparing an aromatic halide and aromatic amine to which a siloxane-containing group is bonded; and constructing a triarylamine derivative by using the halide or amine as a building block may be adopted. Of the latter methods, a production method by aromatic amination, that is, by reacting an aromatic amine derivative, to which a siloxane-containing group is bonded, with an aromatic halide in the presence of a transition metal catalyst is preferred.

In the method for producing a compound represented by the general formula (1) of the present invention, various combinations are contemplated depending on the position of the siloxane-containing group. First, the method for producing a fluorescent compound of the general formula (1) is described, wherein n is 1, 3, or 5, and any of $R^4$ is a siloxane-containing group represented by the general formula (3). The method for producing the fluorescent compound having the characteristics is herein referred to as "Production Method I."

Production Method I includes a step of reacting an amine compound represented by the above-described general formula (4) with an aromatic halogen compound represented by the above-described general formula (5) in the presence of a transition metal catalyst.

In the above-described general formula (4), $R^{4a}$ is identical to $R^4$ in the general formula (1). Thus, in the fluorescent compound represented by the general formula (1), which is the target to be produced, $R^{4a}$ corresponding to the site to which a siloxane-containing group is introduced have to be a siloxane-containing group. Alternatively, if a plurality of different types of $R^4$ are present in the fluorescent compound represented by the general formula (1), which is the target to be produced, $R^{4a}$ in the starting material amine compound represented by the general formula (4) are determined so as to correspond to the plurality of different types of $R^4$.

The amine compound represented by the general formula (4) can be synthesized as appropriate according to a conventional method by those skilled in the art.

In the above-described formula (5), $R^{1a}$ to $R^{4a}$ are each identical to $R^1$ to $R^4$ in the formula (1). If a plurality of different types of $R^1$ to $R^4$ are present in the fluorescent compound represented by the general formula (1), which is the target, $R^{1a}$ to $R^{4a}$ in the starting material amine compound represented by the general formula (4) are determined so as to correspond to the plurality of different types of $R^1$ to $R^4$. $Z^a$ is a halogen atom, such as Cl, Br, and I, preferably Br and I. $X^a$ is the same substituent as X defined in the general formula (1).

o represents an integer of 0 to 2, and satisfies, together with n in the general formula (1), o=(n−1)/2. That is, in production by the production method according to the present embodiment, one molecule of the amine compound of the general formula (4) is reacted with two molecules of the aromatic halogen compound represented by the general formula (5) to enable the fluorescent compound represented by the general formula (1) to be produced.

The aromatic halogen compound represented by the above-described general formula (5) can be provided by synthesizing as appropriate by those skilled in the art according to a conventional method.

Subsequently, in the step of reacting the amine compound represented by the general formula (4) with the aromatic halogen compound represented by the general formula (5) in the presence of a transition metal catalyst, examples of the transition metal catalysts to be used include a palladium catalyst, ruthenium catalyst, rhodium catalyst, platinum catalyst, cobalt catalyst, and nickel catalyst. Of these transition metal catalysts, use of a palladium catalyst is preferred.

Specific examples of palladium catalysts include di-μ-chlorobis[(η-allyl)palladium(II)], palladium acetate, tris (dibenzylideneacetone)dipalladium(0), bis(benzonitrile)dichloropalladium(II), trans-dichlorobis(triphenylphosphine)palladium(II), dichloro(η-cycloocta-1,5-diene)palladium(II), trans-di-μ-bromo-bis[o-(dimesitylphosphino)-3,5-dimethylbenzyl]dipalladium(II), trans-di-μ-chloro-bis[o-(dimesitylphosphino)-3,5-dimethylbenzyl]dipalladium(II), trans-di-μ-iodo-bis[o-(dimesitylphosphino)-3,5-dimethylbenzyl]dipalladium(II), trans-di-μ-acetate-bis[o-(t-butyl-o-tolylphoshino)benzyl]dipalladium(II), trans-di-μ-acetate-bis[o-(di-t-butylphosphino)benzyl]dipalladium(II), and trans-di-μ-acetate-bis[o-(di-o-tolylphoshino)benzyl]dipalladium(II).

Although not particularly limited, the amount of the transition metal catalyst to be used is preferably in the range of 0.000001 to 0.01 moles and more preferably in the range of 0.00001 to 0.001 moles relative to one mole of the amine compound represented by the general formula (4).

In the above-described Production Method I, ligands may be added when the reaction is performed. Examples of such ligands include phosphorus compounds, such as 1,1'-bis(diphenylphosphino)ferrocene, 2-di-tert-butylphosphino-2'-methylbiphenyl, 2-(di-tert-butylphosphino)biphenyl, triphenylphosphine, tri-o-tolylphosphine, tributylphosphine, tri-tert-butylphosphine, tricyclohexylphosphine, di-tert-butylphosphinobiphenyl, dicyclohexylphosphinobiphenyl, and triphenyl phosphite. The amount of these ligands to be used is preferably 0.5 to 2 equivalents and more preferably 0.8 to 1.5 equivalents relative to the transition metal atom to be added as the catalyst. The ligands can be added concurrently with addition of the transition metal catalyst.

In Production Method I, a base is preferably added when the reaction is performed. Examples of the base include inorganic salts, such as sodium hydroxide, potassium hydroxide, sodium carbonate, potassium carbonate, cesium carbonate, sodium hydrogen carbonate, and potassium hydrogen carbonate, metal alkoxides, such as sodium methoxide, potassium methoxide, sodium ethoxide, and potassium ethoxide, organic bases such as methylamine, diethylamine, triethylamine, and pyridine. The amount of the base to be used is preferably 0.1 to 10 moles and more preferably 1 to 3 moles relative to one mole of the amine compound represented by the general formula (4). The base is preferably added concurrently with addition of the catalyst and ligands.

The compounding ratio between the amine compound represented by the general formula (4) and the aromatic halogen compound represented by the general formula (5) at the time of reaction is not particularly limited. From the viewpoint of reactivity and productivity, the amount of the aromatic halogen compound represented by the general formula (5) is preferably 1.5 to 4 moles and more preferably 2.0 to 3.0 moles per one mole of the amine compound represented by the general formula (4).

The reaction temperature of Production Method I is preferably 0 to 300° C. and more preferably 80 to 150° C. The reaction time is preferably 0.1 to 20 hours and more preferably 1 to 3 hours. However, the reaction temperature and reaction time can be determined as appropriate by those skilled in the art and are not limited to the above-described ranges.

Reaction solvents, such as ether-based and hydrocarbon-based solvents, and aprotic polar solvents can be used. Specific examples of the solvents include pentane, hexane, diethylether, tetrahydrofuran, dioxane, toluene, xylene, mesitylene, acetonitrile, N,N-dimethylformamide, N,N-dimethylacetamide or mixtures of these solvents. Of these, use of toluene, xylene, and mesitylene is particularly preferred.

The fluorescent compound represented by the general formula (1) that has been produced according to the above-described production method can be purified by the previously described purification method.

Subsequently, the method for producing the fluorescent compound of the general formula (1) is described, wherein at least one of $R^2$ is an amine-containing group represented by the general formula (2), and at least one of $R^5$ is a siloxane-containing group represented by the general formula (3). The method for producing the fluorescent compound having the characteristics is herein referred to as "Production Method II."

Production Method II includes a step of reacting an amine compound represented by the above-described general formula (6) with an aromatic halogen compound represented by the above-described general formula (7) in the presence of a transition metal catalyst.

In the general formula (6), $R^{5b}$ are identical to $R^5$ in the general formula (2), and any of $R^{5b}$ is the siloxane-containing group represented by the general formula (3). Thus, in the fluorescent compound represented by the general formula (1), which is the target to be produced, $R^{5b}$ corresponding to the site to which a siloxane-containing group is introduced have to be a siloxane-containing group. Alternatively, if a plurality of different types of $R^5$ are present in the general formula (2), which is the target to be produced, $R^{5b}$ in the starting material amine compound represented by the general formula (6) are determined so as to correspond to the plurality of different types of $R^5$.

The amine compound represented by the general formula (6) can be provided by synthesizing as appropriate by those skilled in the art according to a conventional method.

In the general formula (7), $R^{1b}$ to $R^{4b}$ are identical to $R^1$ to $R^4$ in the general formula (1). Again, if a plurality of different types of $R^1$ to $R^4$ are present in the fluorescent compound represented by the general formula (1), which is the target, $R^{1b}$ to $R^{4b}$ in the starting material aromatic halogen compound represented by the general formula (7) are determined so as to correspond to the plurality of different types of $R^1$ to $R^4$, with the proviso that at least one of $R^{2b}$ represents a substituent represented by the general formula (8). Again, in the fluorescent compound represented by the general formula (1), which is the target to, $R^{2b}$ that corresponds to $R^2$ to which an amine-containing group represented by the general formula (2) is introduced has to be a substituent represented by the general formula (8). $X^b$ is identical to X in the general formula (1). $n^b$ is identical to n in the general formula (1).

In the general formula (8), $R^{6b}$ is identical to $R^6$ in the general formula (2). If a plurality of different types of $R^6$ are present in the general formula (2), which is the target to be produced, $R^{6b}$ in the starting material, that is, the general formula (8) are determined so as to correspond to the plurality of different types of $R^6$. $m^b$ is identical to m in the general formula (2). $Z^b$ is a halogen atom, such as Cl, Br, and I, preferably Br or I.

The aromatic halogen compound represented by the above-described general formula (7) can be provided by synthesizing as appropriate by those skilled in the art according to a conventional method.

Also in Production Method II, the reaction can be performed under almost the same conditions and in the same way as Production Method I except the above-described starting material. In the step of reacting the amine compound represented by the general formula (6) with the aromatic halogen compound represented by the general formula (7) in the presence of a transition metal catalyst, the transition metal catalyst similar to those described in the above-described Production Method I can be used. The amount of the catalyst to be used is preferably 0.000001 to 0.01 moles and more preferably in the range of 0.00001 to 0.001 relative to one mole of the aromatic halogen compound represented by the general formula (7).

Also in Production Method II, a ligand similar to those described as in the above-described Production Method I can be used. Similarly to that described in Production Method I, the amount of the ligand to be used is preferably 0.5 to 2 equivalents and more preferably 0.8 to 1.5 equivalents relative to the transition metal atom in a compound added as the catalyst.

Also in Production Method II, it is preferable to additively add a base in the step of reacting the amine compound represented by the general formula (6) with the aromatic halogen compound represented by the general formula (7) in the presence of a transition metal catalyst. A base similar to those described as in the above-described Production Method I can be used. The amount of the base to be used is preferably 0.1 to 10 moles and more preferably 1 to 3 moles relative to one mole of the compound of the general formula (7). The base can be added at the time similar to the one described in the above-described Production Method I.

The compounding ratio between the amine compound represented by the general formula (6) and the aromatic halogen compound by the general formula (7) is not particularly limited. From the viewpoint of reactivity and productivity, the amount of the amine compound represented by the general formula (6) is preferably 1.5 to 4 moles and more preferably 2.0 to 3.0 moles relative to one mole of the aromatic halogen compound represented by the general formula (7).

The reaction temperature of Production Method II is also preferably 0 to 300° C. and more preferably 80 to 150° C. The reaction time is preferably 0.1 to 20 hours and more preferably 1 to 3 hours. However, the reaction temperature and reaction time can be determined as appropriate by those skilled in the art and are not limited to the above-described ranges. A reaction solvent similar to those described as in the above-described Production Method 1 can be used.

The fluorescent compound represented by the general formula (1) that has been produced according to Production Method II can be purified by the previously-described purification method.

The method for producing a fluorescent compound of the general formula (1) is described, wherein n is 0, and at least one of $R^2$ is a siloxane-containing group represented by the general formula (3). The method for producing the fluorescent compound having the characteristics is herein referred to as "Production Method III."

Production Method III includes a step of reacting an amine compound represented by the general formula (10) with an aromatic halogen compound represented by the general formula (9) in the presence of a transition metal catalyst.

In the general formula (9), $X^c$ are each identical to X in the general formula (1), and $Z^c$ are halogen atoms such as Cl, Br, and I, preferably Br or I. The aromatic halogen compound represented by the above-described general formula (9) can be provided by synthesizing as appropriate by those skilled in the art according to a conventional method.

In the general formula (10), $R^{1c}$ and $R^{2c}$ are identical to $R^1$ and $R^2$ in the general formula (1), respectively. If a plurality of different types of $R^1$ and $R^2$ are present in the fluorescent compound represented by the general formula (1), which is the target, $R^{1c}$ and $R^{2c}$ in the starting material amine compound represented by the general formula (10) are determined so as to correspond to the plurality of different types of $R^1$ and $R^2$. In the fluorescent compound represented by the general formula (1), which is the target to be produced, $R^{2c}$ in the general formula (10) of the starting material, which correspond to the site to which a siloxane-containing group is introduced, have to be siloxane-containing groups. The amine compound represented by the general formula (10) can be provided by synthesizing as appropriate by those skilled in the art according to a conventional method.

Also in Production Method III, reaction can be performed under almost the same conditions and in the same way as Production Method I or Production Method II except the above-described starting material. The transition metal catalyst and the amount of the transition metal catalyst to be used, the ligand and the amount of the ligand to be used, the base and the amount of the base to be used, the solvents, and the reaction conditions used in Production Method III may be the same as those in Production Method I or Production Method II. The fluorescent compound represented by the general formula (1) that has been produced according to Production Method III can be purified by the previously-described purification method.

Next, the fluorescent resin composition according to another embodiment of the present invention is described. The fluorescent resin composition according to the present embodiment includes the fluorescent compound of the present invention and a resin.

The fluorescent compound of the present invention, which is represented by the general formula (1), is as described in the above-described embodiment. The fluorescent resin composition according to the present embodiment may include one or more fluorescent compounds represented by the general formula (1). The composition may further include a fluorescent compound having a structure other than the general formula (1), as long as the composition contains at least one fluorescent compound represented by the general formula (1).

Examples of the resin to be a matrix in the fluorescent resin composition include thermoplastic or thermosetting resins such as polyethylenes, polypropylenes, polystyrenes, cycloolefin polymers, polyacrylates, polyvinyl chloride, polycarbonates, polyesters, polyamides, polyimides, polyvinyl alcohols, silicone resins, ethylene-vinyl alcohol copolymer resins, ethylene-vinyl acetate copolymer resins, ABS resins, epoxy resins, phenol resins, melamine resins, and polyurethanes, and elastomers such as natural rubbers, nitrile rubbers, urethane rubbers, EPDMs, styrene-butadiene rubbers, fluorine rubbers, and silicone rubbers, but are not limited to particular resins. In particular, silicone resins such as silicone oils, silicone rubbers, silicone resins, and silicone gels are preferred.

The fluorescent resin composition of the present invention may be in any state such as liquid, solid, rubber and gel. The state of the fluorescent resin composition can be adjusted as appropriate by those skilled in the art, depending on the state of the matrix resin or with optional ingredients described below. Additionally, it is preferred that the fluorescent compound be distributed homogeneously in the fluorescent resin composition of the present invention, without aggregating. To distribute the fluorescent compound homogeneously, the method for producing the fluorescent resin composition preferably includes a step of heating or slowly stirring to achieve homogeneous distribution.

In the fluorescent resin composition of the present invention, although the content of the fluorescent compound is freely selected, the content is, for example, 0.001 to 10% by mass, preferably 0.01 to 5% by mass, and more preferably 0.1 to 5% by mass on the basis of the overall composition. It is preferred to determine the content of the fluorescent compound in a range in which the compound is compatible with the matrix resin. The content of the fluorescent compound in the fluorescent resin composition depends on the properties of the fluorescent compound and the matrix resin. If the content of the fluorescent compound is too high, the fluorescence intensity may be decreased due to concentration quenching. In contrast, if the content is too low, the fluorescence intensity may become insufficient.

The fluorescent resin composition according to the present embodiment may include optional ingredients in addition to the fluorescent compound and the resin. Examples of the optional ingredients include solvents, such as water, methanol, ethanol, hexane, isooctane, decane, toluene, xylene, dimethylformamide, dimethylacetamide, methylpyrrolidone, and dimethyl sulfoxide; fillers, such as silica gel, titanium oxide, zinc oxide, carbon, and magnesium hydroxide; silicon compounds, such as silane coupling agents, tetramethoxysilane, tetraethoxysilane, hexamethyldisiloxane, and decamethylcyclopentasiloxane; radical polymerization initiators, such as azobisisobutyronitrile and benzoyl peroxide; photopolymerization initiators, such as 2-hydroxy-2-methylpropiophenone and diphenyl iodonium hexafluorophosphate, metal compounds, such as chloroplatinic acid, platinum (0) divinyl tetramethyldisiloxane complexes, benzylidene dichlorobis(tricyclohexylphosphine)ruthenium; fibers, such as glass fiber and carbon fiber; ultraviolet absorbents and light stabilizers, such as benzophenone derivatives and hindered amine compounds; plasticizers, such as phthalate esters and adipate esters; and flame retardants such as phosphate ester.

The content of these optional ingredients can be determined freely in a range in which the luminescent properties of the composition is not inhibited. The composition may usually contain the optional ingredients in the range of 0.01 to 80% by mass on the basis of the overall fluorescent resin composition, but this range is not limited.

Subsequently, the fluorescent resin composition according to the present embodiment is described from the viewpoint of the production method. The method for producing the fluorescent resin composition includes a step of mixing a fluorescent compound and a resin. Examples of the step of mixing the fluorescent compound and the resin include kneading the resin and the fluorescent compound to disperse the fluorescent compound. Additionally, included are a step of preliminarily mixing and dissolving a fluorescent compound in a liquid resin monomer or prepolymer followed by addition polymerization or polycondensation, and a step of dissolving a fluorescent compound in resin varnish. Those skilled in the art would be able to perform any of the steps according to a conventional technique.

In the fluorescent resin composition according to the present embodiment, constituents, that is, a fluorescent compound and a resin, are highly compatible, so that a colored fluorescent resin composition is obtained without loss of transparency of the resin itself. Thus, the composition can be widely used in various applications such as fluorescent ink, wavelength converting materials, and dye lasers.

Hereinafter, the present invention will be explained based on Examples and Comparative Examples. However, it should not be construed that the present invention is limited to Examples.

EXAMPLES

Subsequently, the present invention is further described specifically based on Examples and Comparative Example, but it is not limited to any of the following Examples. In the following structural formula, Me represents a methyl group.

Example 1

Synthesis of N,N-bis[4'-(N',N'-di-4-tolylamino)biphenyl-4-yl]-3-(1-trimethylsiloxy-1,3,3,3-tetramethyldisiloxan-1-yl)aniline (Compound 1)

A 100 ml three-neck flask attached with a reflux condenser and a stirrer was nitrogen-purged. To this flask, 921.1 mg (2.15 mmol) of 4'-(N,N-di-4-tolylamino)-4-bromobiphenyl, 315.5 mg (1.09 mmol) of 3-(1-trimethylsiloxy-1,3,3,3-tetramethyldisiloxan-1-yl)aniline, 460.6 mg (4.79 mmol) of sodium-tert-butoxide, 82.1 mg (0.15 mmol) of 1,1-bis(diphenylphosphino)ferrocene, 77.1 mg (0.074 mmol) of tris(dibenzylideneacetone)(chloroform)dipalladium(0) and 8 ml of mesitylene were charged and stirred at 115° C. for 1.5 hours. After the obtained solution was concentrated under reduced pressure and water and toluene were added thereto, the organic layer was extract by separating operation. The obtained solution was dried over magnesium sulfate and concentrated with a rotary evaporator under reduced pressure. Then, purification using silica gel column chromatography and preparative liquid chromatography gave 704.9 mg of a light yellow solid.

As result of the NMR spectrum and MALDI-TOFMS spectrum measurements of this solid, it was confirmed that the solid was N,N-bis[4'-(N',N'-di-4-tolylamino)biphenyl-4-yl]-(1-trimethylsilyloxy-1,3,3,3-tetramethyldisiloxan-1-yl) aniline.

$^1$H-NMR (600 MHz, δ in CDCl$_3$): 0.03 (s, 18H), 0.23 (s, 3H), 2.32 (s, 12H), 7.01-7.10 (m, 20H), 7.12-7.29 (m, 7H), 7.32 (brs, 1H), 7.39-7.46 (m, 8H) MALDI-TOFMS 1007.4 (M$^+$)

The structure of Compound 1 produced according to Example 1 is shown in the following formula (11).

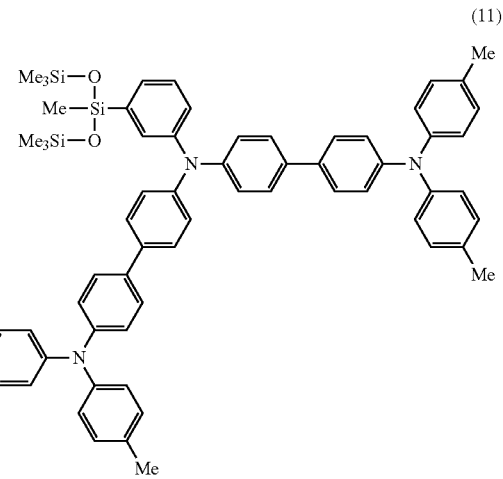

(11)

The ultraviolet-visible absorption spectrum and the fluorescent spectrum of Compound 1 were measured in ethanol. The longest absorption maximum wavelength was 359 nm, the molar absorbance coefficient was 6.50×10$^4$, and the maximum fluorescent wavelength was 410 nm (excitation wavelength: 359 nm).

Example 2

Synthesis of N,N'-bis[phenyl-3-(1-trimethylsoxy-1,3,3,3-tetramethyldisiloxan-1-yl) phenylaminobiphenyl-4'-yl]-N,N-diphenylbenzidine (Compound 2)

A 100 ml three-neck flask attached with a reflux condenser and a stirrer was nitrogen-purged. To this flask, 386.2 mg (0.48 mmol) of N,N'-bis(4'-bromobiphenyl-4-yl)-N,N'-diphenylbenzidine, 409.4 mg (1.05 mmol) of phenyl-3-(1-trimethylsiloxy-1,3,3,3-tetramethyldisiloxan-1-yl)amine, 214.4 mg (2.23 mmol) of sodium-tert-butoxide, 61.9 mg (0.11 mmol) of 1,1-bis(diphenylphosphino)ferrocene, 50.1 mg (0.048 mmol) of tris(dibenzylideneacetone)(chloroform)dipalladium(0), and 8 ml of mesitylene were charged and stirred at 110° C. for 3.5 hours. After the obtained solution was concentrated under reduced pressure and water and toluene were added thereto, the organic layer was extract by separating operation. The obtained solution was dried over magnesium sulfate and concentrated with a rotary evaporator under reduced pressure. Then, purification using silica gel column chromatography and preparative liquid chromatography gave 437.4 mg of a light yellow solid.

As result of the NMR spectrum and MALDI-TOFMS spectrum measurements of this solid, it was confirmed that the solid was N,N'-bis[phenyl-3-(1-trimethylsiloxy-1,3,3,3-tetramethyldisiloxan-1-yl)phenylaminobiphenyl-4'-yl]-N,N'-diphenylbenzidine, $^1$H-NMR (600 MHz, δ in CDCl$_3$): 0.03 (s, 36H), 0.22 (s, 6H), 6.98-7.32 (m, 40H), 7.42-7.50 (m, 12H) MALDI-TOFMS m/z: 1415.6 (M$^+$)

The structure of Compound 2 produced according to Example 2 is shown in the following formula (12).

The ultraviolet-visible absorption spectrum and the fluorescent spectrum of Compound 2 were measured in ethanol. The longest absorption maximum wavelength was 359 nm, the molar absorbance coefficient was $7.88 \times 10^4$, and the maximum fluorescent wavelength was 410 nm (excitation wavelength: 359 nm).

Example 3

Synthesis of N,N-bis[4'-(N'-phenyl-N'-4'-diphenylaminobiphenyl-4-yl) biphenyl-4-yl]-3-(1-trimethylsiloxy-1,3,3,3-tetramethyldisiloxan-1-yl)aniline (Compound 3)

A 100 ml three-neck flask attached with a reflux condenser and a stirrer was nitrogen-purged. To this flask, 665.8 mg (1.03 mmol) of N-(4'-bromobiphenyl-4-yl)-N',N',N'-triphenylbenzidine, 108.4 mg (0.45 mmol) of phenyl-3-(1-trimethylsiloxy-1,3,3,3-tetramethyldisiloxan-1-yl)amine, 211.5 mg (2.20 mmol) of sodium-tert-butoxide, 21.0 mg (0.10 mmol) of tri-tert-butylphosphine, 42.1 mg (0.041 mmol) of tris(dibenzylideneacetone)(chloroform)dipalladium(0), and 5 ml of mesitylene were charged, and stirred at 120° C. for 3.5 hours. After the obtained solution was concentrated under reduced pressure and water and toluene were added thereto, the organic layer was extract by separating operation. The obtained solution was dried over magnesium sulfate and concentrated with a rotary evaporator under reduced pressure. Then, purification using silica gel column chromatography and preparative liquid chromatography gave 353.2 mg of a light yellow solid.

As result of the NMR spectrum and MALDI-TOFMS spectrum measurements of this solid, it was confirmed that

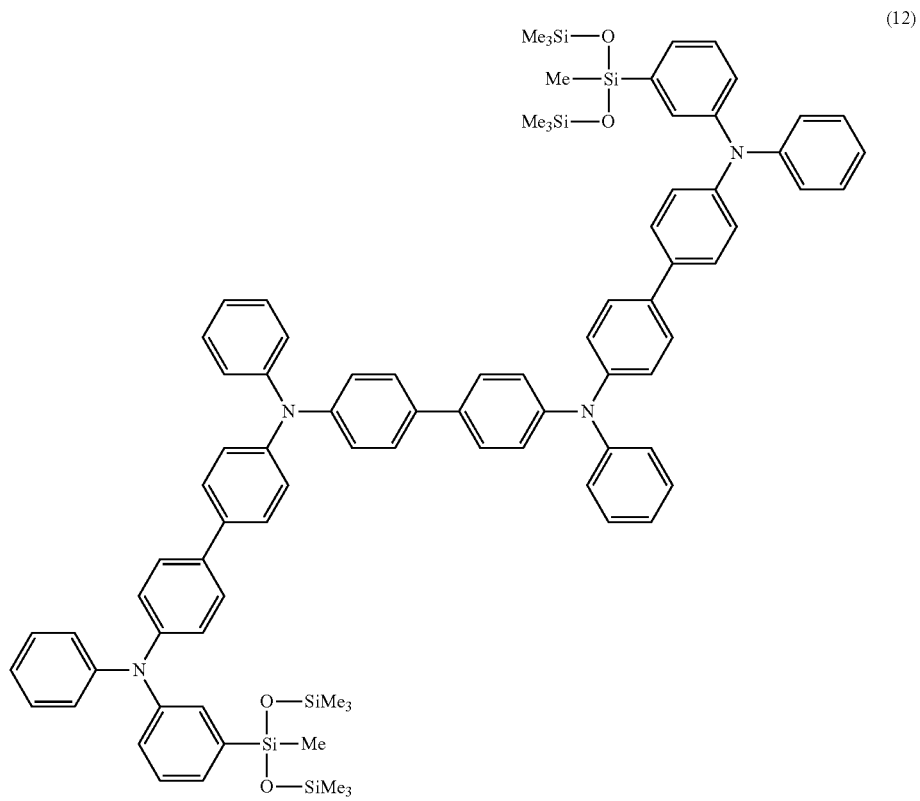 [SMILES: C[Si](C)(C)O[Si](C)(O[Si](C)(C)C)c1cccc(N(c2ccccc2)c2ccc(-c3ccc(N(c4ccccc4)c4ccc(-c5ccc(N(c6ccccc6)c6ccc(-c7ccc(N(c8ccccc8)c8cccc([Si](C)(O[Si](C)(C)C)O[Si](C)(C)C)c8)cc7)cc6)cc5)cc4)cc3)cc2)c1]

(12)

the solid was N,N-bis[4'-(N'-phenyl-N-4'-diphenylaminobiphenyl-4-yl)biphenyl-4-yl]-3-(1-trimethylsiloxy-1,3,3,3-tetramethyldisiloxan-1-yl)aniline.

$^1$H-NMR (600 MHz, δ in CDCl$_3$): 0.03 (s, 18H), 0.23 (s, 3H), 7.00-7.07 (m, 28H), 7.09-7.23 (m, 28H), 7.24-7.32 (m, 16H), 7.43-7.51 (m, 16H) MALDI-TOFMS m/z: 1437.6 (M$^+$)

The structure of Compound 3 produced according to Example 3 is shown in the following formula (13).

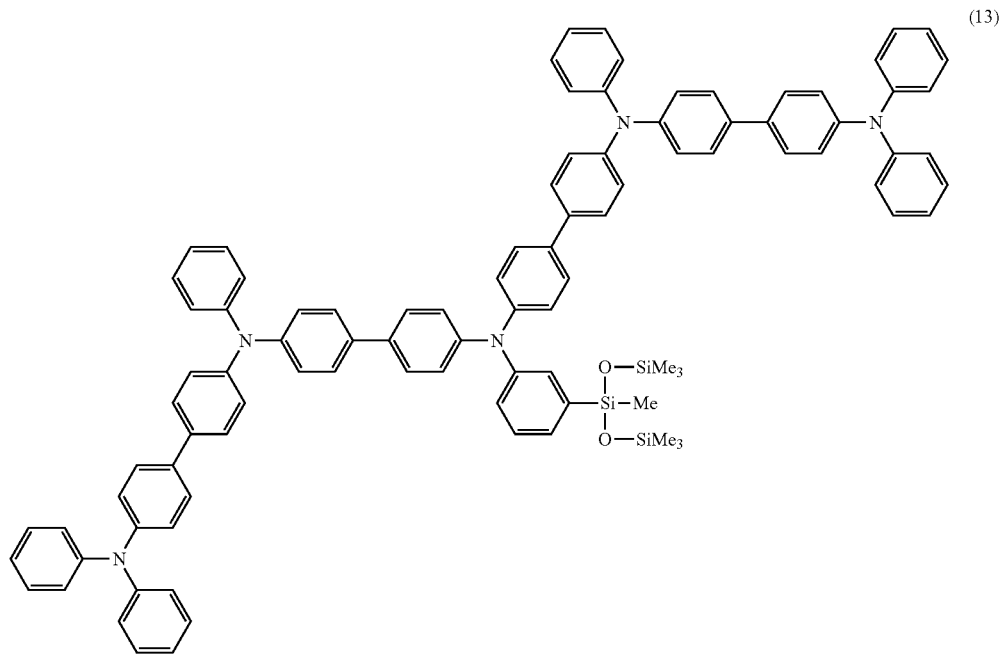 [SMILES: C[Si](C)(C)O[Si](C)(O[Si](C)(C)C)c1cccc(N(c2ccc(-c3ccc(N(c4ccccc4)c4ccc(-c5ccc(N(c6ccccc6)c6ccccc6)cc5)cc4)cc3)cc2)c2ccc(-c3ccc(N(c4ccccc4)c4ccc(-c5ccc(N(c6ccccc6)c6ccccc6)cc5)cc4)cc3)cc2)c1]

The ultraviolet-visible absorption spectrum and the fluorescent spectrum of Compound 3 were measured in tetrahydrofuran. The longest absorption maximum wavelength was 363 nm, the molar absorbance coefficient was 2.65×10$^4$, and the maximum fluorescent wavelength was 413 nm (excitation wavelength: 363 nm).

Example 4

Synthesis of N,N-bis[4'-(N'-phenyl-N'-4'-diphenylaminobiphenyl-4-yl)biphenyl-4-yl]-3-(pentamethyldisiloxan-1-yl)aniline (Compound 4)

A 100 ml three-neck flask attached with a reflux condenser and a stirrer was nitrogen-purged. To this flask, 583.2 mg (0.90 mmol) of N-(4'-bromobiphenyl-4-yl)-N',N',N'-triphenylbenzidine, 118.7 mg (0.41 mmol) of phenyl-3-(pentamethyldisiloxan-1-yl)amine, 203.6 mg (2.12 mmol) of sodium-tert-butoxide, 14.0 mg (0.069 mmol) of tri-tert-butylphosphine, 31.4 mg (0.030 mmol) of tris(dibenzylideneacetone)(chloroform)dipalladium(0), and 5 ml of mesitylene were charged, and stirred at 125° C. for 1.5 hours. After the obtained solution was concentrated under reduced pressure and water and toluene were added thereto, the organic layer was extract by separating operation. The obtained solution was dried over magnesium sulfate and concentrated with a rotary evaporator under reduced pressure. Then, purification using silica gel column chromatography and preparative liquid chromatography gave 308.1 mg of a light yellow solid.

As result of the NMR spectrum and MALDI-TOFMS spectrum measurements of this solid, it was confirmed that the solid was N,N-bis[4'-(N'-phenyl-N'-4'-diphenylaminobiphenyl-4-yl)biphenyl-4-yl]-3-(pentamethyldisiloxan-1-yl)aniline.

$^1$H-NMR (600 MHz, δ in CDCl$_3$): 0.02 (s, 9H), 0.28 (s, 6H), 7.11-7.24 (m, 28H), 7.25-7.32 (m, 14H), 7.35-7.37 (m, 1H), 7.44-7.52 (m, 16H) MALDI-TOFMS m/z: 1364.7 (M$^+$)

The structure of Compound 4 produced according to Example 4 is shown in the following formula (14).

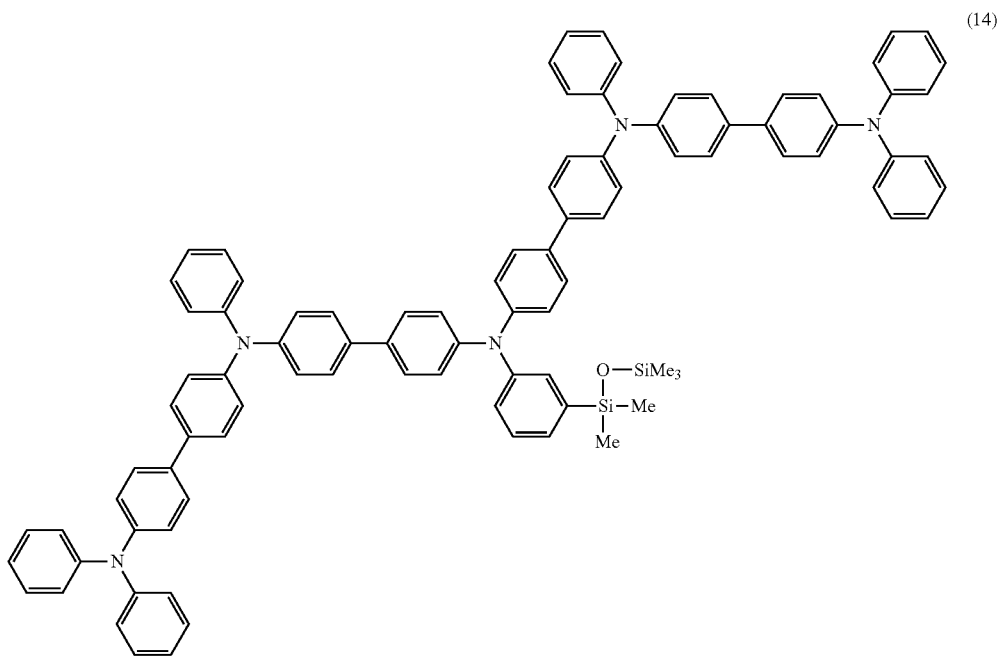 [SMILES: C[Si](C)(C)O[Si](C)(C)c1cccc(N(c2ccc(-c3ccc(N(c4ccccc4)c4ccc(-c5ccc(N(c6ccccc6)c6ccccc6)cc5)cc4)cc3)cc2)c2ccc(-c3ccc(N(c4ccccc4)c4ccc(-c5ccc(N(c6ccccc6)c6ccccc6)cc5)cc4)cc3)cc2)c1]

(14)

The ultraviolet-visible absorption spectrum and the fluorescent spectrum of Compound 4 were measured in tetrahydrofuran. The longest absorption maximum wavelength was 363 nm, the molar absorbance coefficient was $2.83 \times 10^4$, and the maximum fluorescent wavelength was 413 nm (excitation wavelength: 363 nm)

Example 5

Synthesis of N,N'-diphenyl-N,N'-di-[3-(1-trimethylsiloxy-1,3,3,3-tetramethyldisiloxan-1-yl)phenyl]-benzidine A 100 ml three-neck flask attached with a reflux condenser and a stirrer was nitrogen-purged. To this flask, 71.3 mg (0.23 mmol) of 4,4'-dibromobiphenyl, 197.3 mg (0.51 mmol) of phenyl-3-(1-trimethylsiloxy-1,3,3,3-tetramethyldisiloxan-1-yl)phenylamine, 150.8 mg (0.63 mmol) of sodium-tert-butoxide, 7.5 mg (0.037 mmol) of tri-tert-butylphosphine, 24.8 mg (0.024 mmol) of tris(dibenzylideneacetone)(chloroform) dipalladium(0), and 3 ml of mesitylene were charged, and stirred at 110° C. for 7 hours. After the obtained solution was concentrated under reduced pressure and water and toluene were added thereto, the organic layer was extract by separating operation. The obtained solution was dried over magnesium sulfate and concentrated with a rotary evaporator under reduced pressure. Then, purification using silica gel column chromatography and preparative liquid chromatography gave 332.0 mg of a colorless liquid.

As result of the MALDI-TOFMS spectrum measurements of this liquid, it was confirmed that the liquid was N,N'-diphenyl-N,N'-di-[3-(1-trimethylsiloxy-1,3,3,3-tetramethyldisiloxan-1-yl)phenyl]-benzidine. MALDI-TOFMS m/z: 929.5 (M+).

The structure of Compound 5 produced according to Example 5 is shown in the following formula (15).

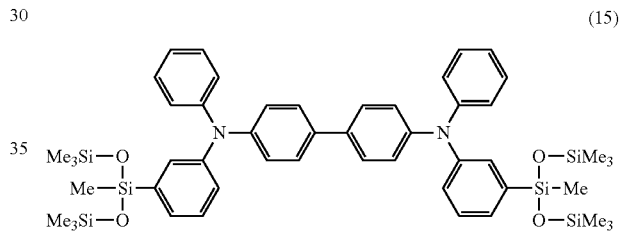

(15)

Example 6

Production of a Silicone Resin Composition Containing Compound 1

Into a glass vial, 10.1 mg of Compound 1 produced in Example 1 was weighed and added with a transparent silicone resin, the SIM-360 base compound (produced by Shin-Etsu Chemical Co., Ltd.) portion-wise at room temperature with stirring. Dissolution was determined when the solution turned transparent. The solubility was calculated to be 1 mmol/L. To this mixture, 10% by mass of a curing agent was added on the basis of the base compound and mixed. After defoaming, the mixture was heated at 150° C. for 30 minutes to be cured, giving a fluorescent silicone resin composition. It was possible to change the concentration of Compound 1 freely as long as the concentration was less than or equal to the above-described concentration.

Example 7

Production of a Silicone Resin Composition Containing Compound 2

The solubility of Compound 2 in the SIM-360 base compound, which was measured as in Example 6, was 0.5 mmol/L. To this mixture, 10% by mass of a curing agent was added on the basis of the base compound and mixed. After defoaming, the mixture was heated at 150° C. for 30 minutes to be cured, giving a fluorescent silicone resin composition. It was possible to change the concentration of Compound 2 freely as long as the concentration was less than or equal to the above-described concentration.

Example 8

Production of a Silicone Resin Composition Containing Compound 3

The solubility of Compound 3 in the SIM-360 base compound, which was measured as in Example 6, was 0.1 mmol/L. To this mixture, 10% by mass of a curing agent was added on the basis of the base compound and mixed. After defoaming, the mixture was heated at 150° C. for 30 minutes to be cured, giving a fluorescent silicone resin composition. It was possible to change the concentration of Compound 3 freely as long as the concentration was less than or equal to the above-described concentration.

Example 9

Production of a Silicone Resin Composition Containing Compound 4

The solubility of Compound 4 in the SIM-360 base compound, which was measured as in Example 6, was 0.1 mmol/L. To this mixture, 10% by mass of a curing agent was added on the basis of the base compound and mixed. After defoaming, the mixture was heated at 150° C. for 30 minutes to be cured, giving a fluorescent silicone resin composition. It was possible to change the concentration of Compound 4 freely as long as the concentration was less than or equal to the above-described concentration.

Comparative Example 1

Measurement of the Solubility of Compound 6 in a Silicone Resin

The structure of the compound 6 used in this Comparative Example 1 is shown in the following formula (16). When the solubility of Compound 6 in the SIM-360 base compound was measured as in Example 6, the mixture became clouded and the compound was not dissolved at all.

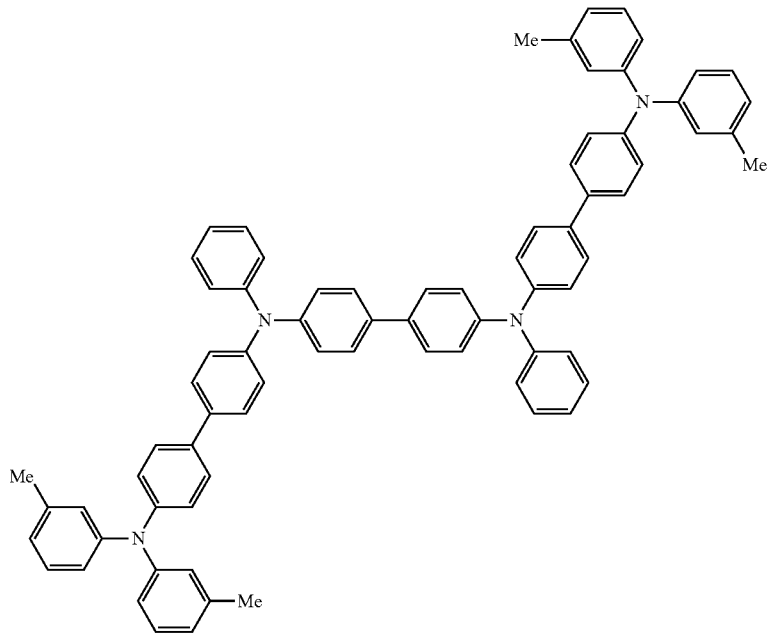

(16)

The fluorescent compound of the present invention is highly useful because the compound enables low polar resins, such as silicone resins, to be colored without loss of transparency, and thus provides highly transparent fluorescent resin compositions. The composition can be used in fluorescent ink, wavelength converting materials, dye lasers, and the like. Since it has a triarylamine skeleton, the fluorescent compound of the present invention can be used as charge transport compounds and luminescent compounds in organic electronic devices such as organic electroluminescent elements.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:
1. A fluorescent compound represented by the following general formula (1):

(1)

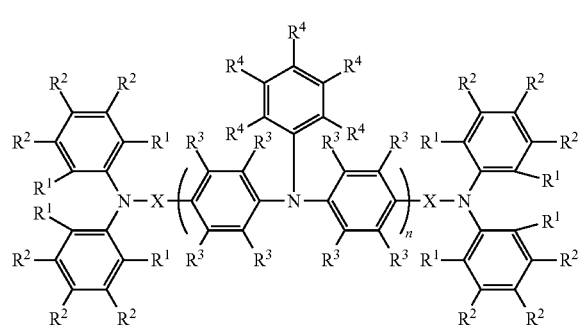

wherein $R^1$ to $R^4$ each independently represent a substituent selected from a linear, branched or cyclic monovalent hydrocarbon group having 1 to 20 carbon atoms, an alkoxy group having 1 to 20 carbon atoms, an aryloxy group having 6 to 20 carbon atoms, a halogen atom, a hydrogen atom, an amino group, a cyano group, an amine-containing group represented by the following general formula (2), and a siloxane-containing group represented by the following general formula (3); or the carbon atoms at the ortho position of the nitrogen atom bonded to X directly bond to each other to form a carbazole ring structure, resulting in that $R^1$ is not present;

with the proviso that when an amine-containing group represented by the general formula (2) as the substituent is not included, at least one of $R^1$ to $R^4$ is a siloxane-containing group represented by the following general formula (3), and that when an amine-containing group represented by the following general formula (2) as the substituent is included, at least one of $R^1$ to $R^6$ is a siloxane-containing group represented by the following general formula (3), each of X may be identical or different, represents a single bond, or a linear, branched or cyclic divalent hydrocarbon group having 1 to 20 carbon atoms, and some of the carbon atoms may be substituted with a heteroatom; and n is an integer of 0 to 5:

(2)

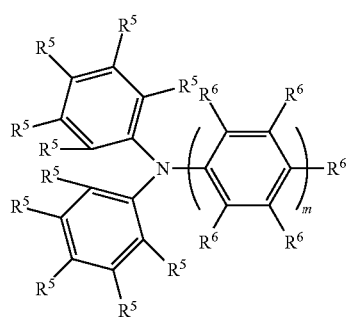

wherein $R^5$ and $R^6$ each independently represent a substituent selected from a linear, branched or cyclic monovalent hydrocarbon group having 1 to 20 carbon atoms, alkoxy group having 1 to 20 carbon atoms, aryloxy group having 6 to 20 carbon atoms, halogen atom, hydrogen atom, amino group, and siloxane-containing group represented by the following general formula (3); and m is 0 or 1;

$$S_x\text{-A-} \quad (3)$$

wherein $S_x$ represents a linear, branched or cyclic organosiloxanyl group having 2 to 10 silicon atoms and a monovalent hydrocarbon group having 1 to 20 carbon atoms bonded to at least one of the silicon atoms; and A represents a single bond, or a linear, branched or cyclic divalent hydrocarbon group having 1 to 20 carbon atoms which may contain at least one of —S— or —$NR^0$—, or a combination thereof, with the proviso that heteroatoms of sulfur and nitrogen are not adjacent to each other except the case where A is a cyclic divalent hydrocarbon group, and $R^0$ is a monovalent hydrocarbon group having 1 to 20 carbon atoms.

2. A fluorescent compound represented by the following general formula (1):

(1)

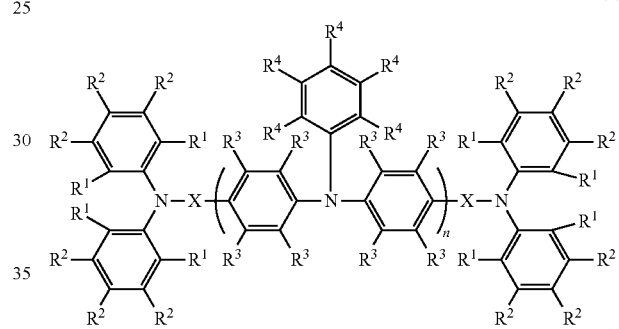

wherein $R^1$ to $R^4$ each independently represent a substituent selected from a linear, branched or cyclic monovalent hydrocarbon group having 1 to 20 carbon atoms, an alkoxy group having 1 to 20 carbon atoms, an aryloxy group having 6 to 20 carbon atoms, a halogen atom, a hydrogen atom, an amino group, a cyano group, an amine-containing group represented by the following general formula (2), and a siloxane-containing group represented by the following general formula (3); or the carbon atoms at the ortho position of the nitrogen atom bonded to X directly bond to each other to form a carbazole ring structure, resulting in that $R^1$ is not present;

with the proviso that when an amine-containing group represented by the general formula (2) as the substituent is not included, at least one of R to $R^4$ is a siloxane-containing group represented by the following general formula (3), and that when an amine-containing group represented by the following general formula (2) as the substituent is included, at least one of $R^1$ to $R^6$ is a siloxane-containing group represented by the following general formula (3);

each of X may be identical or different, represents a single bond, or a linear, branched or cyclic divalent hydrocarbon group having 1 to 20 carbon atoms, and some of the carbon atoms may be substituted with a heteroatom; and n is an integer of 0 to 5:

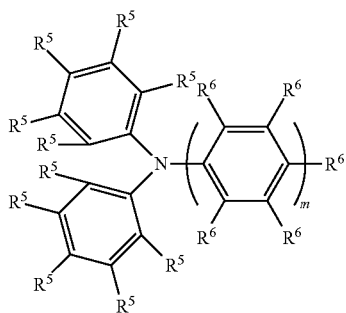

(2)

wherein R⁵ and R⁶ each independently represent a substituent selected from a linear, branched or cyclic monovalent hydrocarbon group having 1 to 20 carbon atoms, alkoxy group having 1 to 20 carbon atoms, aryloxy group having 6 to 20 carbon atoms, halogen atom, hydrogen atom, amino group, and siloxane-containing group represented by the following general formula (3); and m is 0 or 1;

$S_x$-A-  (3)

wherein $S_x$ represents a linear, branched or cyclic organosiloxanyl group having 2 to 10 silicon atoms and a monovalent hydrocarbon group having 1 to 20 carbon atoms bonded to at least one of the silicon atoms; and A represents a single bond, or a linear, branched or cyclic divalent hydrocarbon group having 1 to 20 carbon atoms which may contain at least one of —O—, —S— or —NR⁰—, or a combination thereof, with the proviso that heteroatoms of oxygen, sulfur and nitrogen are not adjacent to each other except the case where A is a cyclic divalent hydrocarbon group, and R is a monovalent hydrocarbon group having 1 to 20 carbon atoms, and wherein, in the general formula (1), n is 1, 3, or 5, and at least one of R⁴ is a siloxane-containing group represented by the general formula (3).

3. A fluorescent compound, represented by the following general formula (1):

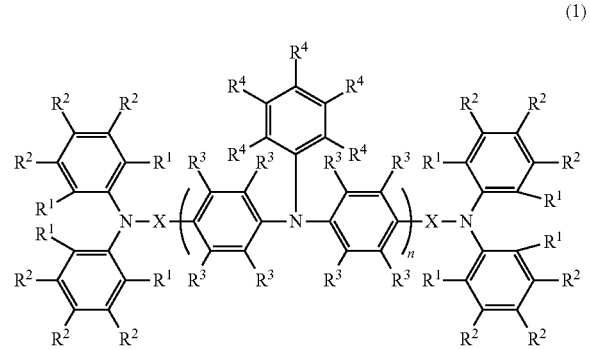

(1)

wherein R¹ to R⁴ each independently represent a substituent selected from a linear, branched or cyclic monovalent hydrocarbon group having 1 to 20 carbon atoms, an alkoxy group having 1 to 20 carbon atoms, an aryloxy group having 6 to 20 carbon atoms, a halogen atom, a hydrogen atom, an amino group, a cyano group, an amine-containing group represented by the following general formula (2), and a siloxane-containing group represented by the following general formula (3); or the carbon atoms at the ortho position of the nitrogen atom bonded to X directly bond to each other to form a carbazole ring structure, resulting in that R¹ is not present:

with the proviso that when an amine-containing group represented by the general formula (2) as the substituent is not included, at least one of R¹ to R⁴ is a siloxane-containing represented by the following general formula (3), and that when an amine-containing group represented by the following general formula (2) as the substituent is included at least one of R¹ to R⁶ is a siloxane-containing group represented by the following general formula (3);

each of X may be identical or different, represents a single bond, or a linear, branched or cyclic divalent hydrocarbon group having 1 to 20 carbon atoms, and some of the carbon atoms may be substituted with a heteroatom; and n is an integer of 0 to 5:

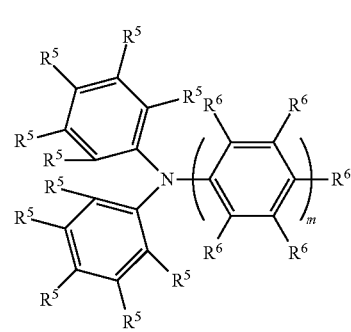

(2)

wherein R⁵ and R⁶ each independently represent a substituent selected from a linear, branched or cyclic monovalent hydrocarbon group having 1 to 20 carbon atoms, alkoxy group having 1 to 20 carbon atoms, aryloxy group having 6 to 20 carbon atoms, halogen atom, hydrogen atom, amino group, and siloxane-containing group represented by the following general formula (3); and m is 0 or 1:

$S_x$-A-  (3)

wherein $S_x$ represents a linear, branched or cyclic or organosiloxanyl group having 2 to 10 silicon atoms and a monovalent hydrocarbon group having 1 to 20 carbon atoms bonded to at least one of the silicon atoms; and A represents a single bond, or a linear, branched or cyclic divalent hydrocarbon group having 1 to 20 carbon atoms which may contain at least one of —O—, —S— or —NR⁰—, or a combination thereof, with the proviso that heteroatoms of oxygen, sulfur and nitrogen are not adjacent to each other except the case where A is a cyclic divalent hydrocarbon group, and R⁰ is a monovalent hydrocarbon group having 1 to 20 carbon atoms, and wherein, in the general formula (1), at least one of R² is an amine-containing group represented by the general formula (2), and at least one of R⁵ is a siloxane-containing group represented by the general formula (3).

4. The fluorescent compound according to claim 1, wherein, in the general formula (1), n is 0, and at least one of R² is a siloxane-containing group represented by the general formula (3).

5. A fluorescent resin composition comprising the fluorescent compound according to claim 1 and a resin.

6. The fluorescent resin composition according to claim 5, wherein the resin is a silicone resin.

7. A method for producing a fluorescent compound according to claim 2, comprising a step of reacting an amine compound represented by the following general formula (4) with an aromatic halogen compound represented by the following general formula (5) in the presence of a transition metal catalyst:

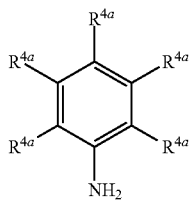
(4)

wherein $R^{4a}$ is identical to $R^4$ in the general formula (1);

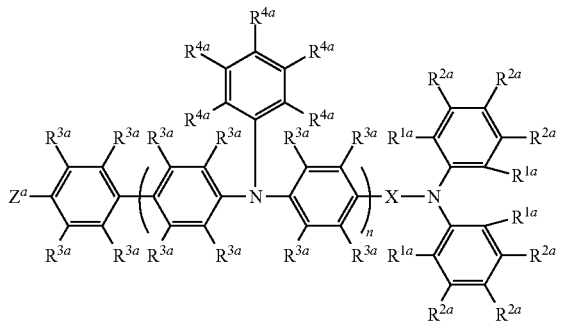
(5)

wherein $R^{1a}$ to $R^{4a}$ are identical to $R^1$ to $R^4$ in the general formula (1), respectively;
$Z^a$ is a halogen atom;
$X^a$ is identical to X in the general formula (1); and
o represents an integer of 0 to 2, and satisfies, together with n in the general formula (1), o=(n−1)/2.

8. A method for producing a fluorescent compound according to claim 3, comprising a step of reacting an amine compound represented by the following general formula (6) with an aromatic halogen compound represented by the following general formula (7) in the presence of a transition metal catalyst:

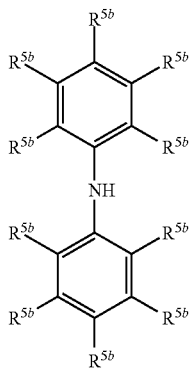
(6)

wherein $R^{5b}$ is identical to $R^5$ in the general formula (2);

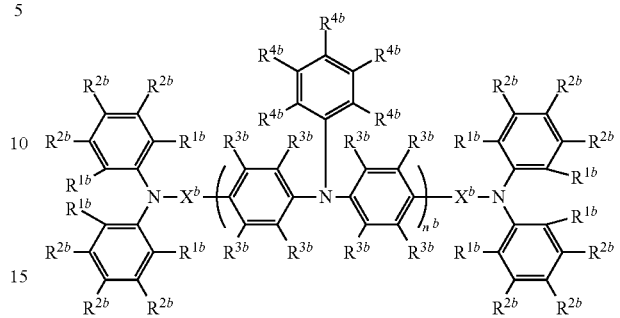
(7)

wherein $R^{1b}$ to $R^{4b}$ are identical to $R^1$ to $R^4$ in the general formula (1), respectively;
$X^b$ is identical to X in the general formula (1); and
$n^b$ is identical to n in the general formula (1), with the proviso that at least one of $R^{2b}$ represents a substituent represented by the general formula (8);

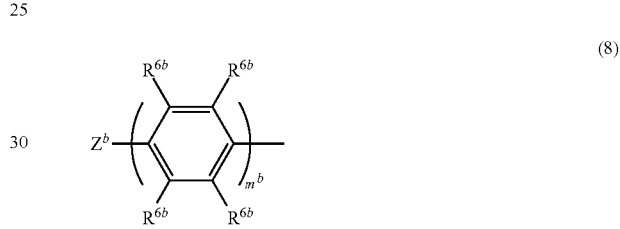
(8)

wherein $R^{6b}$ is identical to $R^6$ in the general formula (2);
$m^b$ is identical to m in the general formula (2); and
$Z^b$ is a halogen atom.

9. A method for producing a fluorescent compound according to claim 4, comprising a step of reacting an amine compound represented by the following general formula (10) with an aromatic halogen compound represented by the following general formula (9) in the presence of a transition metal catalyst:

$$Z^c-X^c-X^c-Z^c \quad (9)$$

wherein $X^c$ is identical to X in the general formula (1); and Z is a halogen atom;

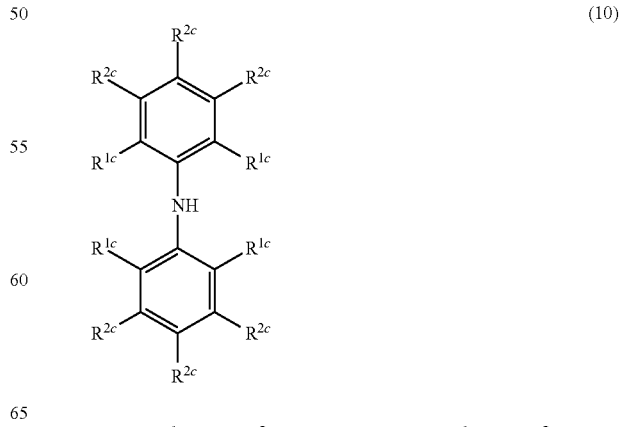
(10)

wherein $R^{1c}$ and $R^{2c}$ are identical to $R^1$ and $R^2$ in the general formula (1), respectively.

10. A fluorescent resin composition comprising the fluorescent compound according to claim 2 and a resin.

11. The fluorescent resin composition according to claim 10, wherein the resin is a silicone resin.

12. A fluorescent resin composition comprising the fluorescent compound according to claim 3 and a resin.

13. The fluorescent resin composition according to claim 12, wherein the resin is a silicone resin.

14. A fluorescent resin composition comprising the fluorescent compound according to claim 4 and a resin.

15. The fluorescent resin composition according to claim 14, wherein the resin is a silicone resin.

* * * * *

UNITED STATES PATENT AND TRADEMARK OFFICE
CERTIFICATE OF CORRECTION

PATENT NO.       : 9,217,071 B2
APPLICATION NO.  : 14/178417
DATED            : December 22, 2015
INVENTOR(S)      : Itoh et al.

It is certified that error appears in the above-identified patent and that said Letters Patent is hereby corrected as shown below:

In the Specification:
Column 22, Line 36: Please correct "TOFMS 1007.4"
to read -- TOFMS m/z: 1007.4 --

Column 27, Line 34: Please correct "363 nm)" to read -- 363 nm). --

In the Claims:
Column 32, Claim 2, Line 57: Please correct "of R to $R^4$" to read -- of $R^1$ to $R^4$ --

Column 33, Claim 2, Line 38: Please correct "and R is" to read -- and $R^0$ is --

Column 34, Claim 3, Line 6: Please correct "present:" to read -- present; --

Signed and Sealed this
Sixteenth Day of August, 2016

Michelle K. Lee
*Director of the United States Patent and Trademark Office*

CERTIFICATE OF CORRECTION (continued)
U.S. Pat. No. 9,217,071 B2

Column 35, Claim 7, Lines 25-37: Please correct the formula below:

" 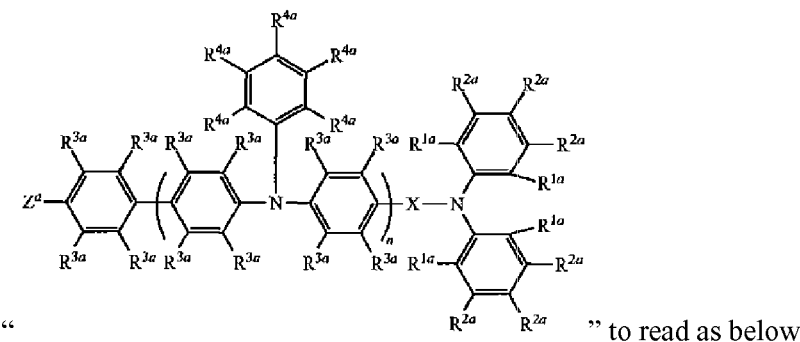 " to read as below

-- 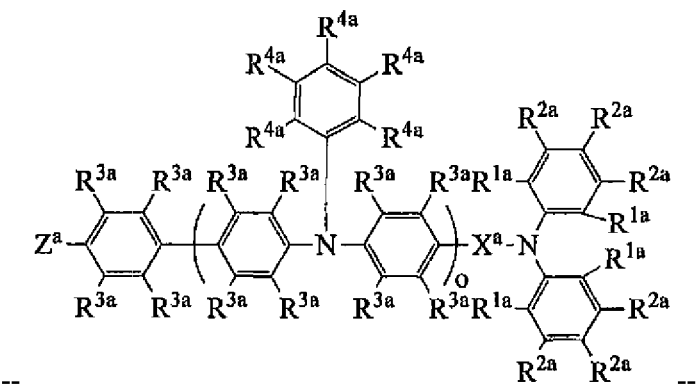 --